United States Patent
Bianchi et al.

(10) Patent No.: US 11,123,235 B2
(45) Date of Patent: *Sep. 21, 2021

(54) ABSORBENT ARTICLE WITH A LOTIONED TOPSHEET

(71) Applicant: The Procter & Gamble Company, Cincinnati, OH (US)

(72) Inventors: Ernesto Gabriel Bianchi, Oberursel (DE); Joerg Endres, Frankfurt (DE); Julien Rene Garcia, Frankfurt (DE); Donald Carroll Roe, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 397 days.

This patent is subject to a terminal disclaimer.

(21) Appl. No.: 16/016,698

(22) Filed: Jun. 25, 2018

(65) Prior Publication Data
US 2019/0000687 A1    Jan. 3, 2019

Related U.S. Application Data

(60) Provisional application No. 62/527,101, filed on Jun. 30, 2017.

(51) Int. Cl.
*A61F 13/532* (2006.01)
*A61F 13/511* (2006.01)
(Continued)

(52) U.S. Cl.
CPC .. *A61F 13/51113* (2013.01); *A61F 13/15203* (2013.01); *A61F 13/496* (2013.01);
(Continued)

(58) Field of Classification Search
CPC .......... A61F 13/51104; A61F 13/51108; A61F 13/5113; A61F 13/533; A61F 13/536;
(Continued)

(56) References Cited

U.S. PATENT DOCUMENTS 3,848,594 A    11/1974    Buell
3,860,003 A    1/1975    Buell
(Continued)

FOREIGN PATENT DOCUMENTS

EP    149880 A2    7/1985
EP    0781537 A1    7/1997
(Continued)

OTHER PUBLICATIONS

International Search Report, PCT/US2018/039273, dated Sep. 7, 2018, 15 pages.
All Office Actions, U.S. Appl. No. 16/018,096.

*Primary Examiner* — Catharine L Anderson
(74) *Attorney, Agent, or Firm* — Wednesday G. Shipp

(57) ABSTRACT

An absorbent article having a longitudinal axis extending in a longitudinal direction and a transversal axis extending in a transversal direction perpendicular to the longitudinal direction. The absorbent article comprises a fluid-permeable topsheet, a lotion on the topsheet having a lotion pattern covering a lotion pattern area, a fluid-impermeable backsheet, and an absorbent core between the topsheet and the backsheet. The core wrap defines a core footprint in a plane parallel to the longitudinal direction and transversal direction. The article comprises an intermediate layer between the topsheet and the absorbent core, the intermediate layer comprising at least one longitudinally-extending channel, preferably at least a pair of longitudinally-extending channels disposed symmetrically on each side of the longitudinal axis. The topsheet is depressed in the channel(s). The lotion-to-channel overlap ratio ranges from 0% to 20% of the area of the channel(s). The lotion-to-channel overlap ratio is the percentage of the channel(s) of the intermediate layer overlapping with the lotion pattern.

20 Claims, 8 Drawing Sheets

(51) Int. Cl.
*A61F 13/537* (2006.01)
*A61F 13/15* (2006.01)
*A61F 13/496* (2006.01)
*A61F 13/512* (2006.01)
*A61F 13/515* (2006.01)
*A61F 13/51* (2006.01)

(52) U.S. Cl.
CPC ........ *A61F 13/515* (2013.01); *A61F 13/5121* (2013.01); *A61F 13/51104* (2013.01); *A61F 13/51108* (2013.01); *A61F 13/51121* (2013.01); *A61F 13/532* (2013.01); *A61F 13/53747* (2013.01); *A61F 2013/15406* (2013.01); *A61F 2013/51019* (2013.01); *A61F 2013/51117* (2013.01); *A61F 2013/53778* (2013.01)

(58) Field of Classification Search
CPC ...... A61F 13/53747; A61F 2013/51117; A61F 2013/53778
See application file for complete search history.

(56) References Cited

U.S. PATENT DOCUMENTS

| | | | |
|---|---|---|---|
| 3,929,135 A | 12/1975 | Thompson | |
| 4,324,246 A | 4/1982 | Mullane et al. | |
| 4,342,314 A | 8/1982 | Radel et al. | |
| 4,463,045 A | 7/1984 | Ahr et al. | |
| 4,515,595 A | 5/1985 | Kievit et al. | |
| 4,609,518 A | 9/1986 | Curro et al. | |
| 4,629,643 A | 12/1986 | Curro et al. | |
| 4,662,875 A | 5/1987 | Hirotsu et al. | |
| 4,695,278 A | 9/1987 | Lawson | |
| 4,699,622 A | 10/1987 | Toussant et al. | |
| 4,710,189 A | 12/1987 | Lash | |
| 4,778,458 A * | 10/1988 | Gronostajski | A61F 5/4401 427/394 |
| 4,795,454 A | 1/1989 | Dragoo | |
| 4,808,178 A | 2/1989 | Aziz et al. | |
| 4,846,815 A | 7/1989 | Scripps | |
| 4,894,060 A | 1/1990 | Nestegard | |
| 4,909,803 A | 3/1990 | Aziz et al. | |
| 4,946,527 A | 8/1990 | Battrell | |
| 4,963,140 A | 10/1990 | Robertson et al. | |
| 5,006,394 A | 4/1991 | Baird | |
| 5,151,092 A | 2/1992 | Buell et al. | |
| 5,137,537 A | 8/1992 | Herron et al. | |
| 5,221,274 A | 6/1993 | Buell et al. | |
| 5,242,436 A | 9/1993 | Weil et al. | |
| 5,348,547 A | 9/1994 | Payne et al. | |
| 5,486,166 A | 1/1996 | Bishop et al. | |
| 5,490,846 A | 2/1996 | Ellis et al. | |
| 5,499,978 A | 3/1996 | Buell et al. | |
| 5,549,791 A | 8/1996 | Herron et al. | |
| 5,591,152 A | 1/1997 | Buell et al. | |
| 5,607,760 A | 3/1997 | Roe | |
| 5,609,587 A | 3/1997 | Roe | |
| 5,643,588 A | 7/1997 | Roe et al. | |
| 5,814,570 A | 9/1998 | Cohen | |
| 5,837,352 A | 11/1998 | English et al. | |
| 5,843,056 A | 12/1998 | Good et al. | |
| 5,968,025 A | 10/1999 | Roe et al. | |
| 6,075,179 A | 6/2000 | McCormack et al. | |
| 6,336,922 B1 | 1/2002 | VanGompel et al. | |
| 6,432,098 B1 | 8/2002 | Kline et al. | |
| 6,632,504 B1 | 10/2003 | Gillespie et al. | |
| 6,645,569 B2 | 11/2003 | Cramer et al. | |
| 6,716,441 B1 | 4/2004 | Osborne et al. | |
| 6,863,933 B2 | 3/2005 | Cramer et al. | |
| 7,112,621 B2 | 9/2006 | Rohrbaugh et al. | |
| 7,744,576 B2 | 6/2010 | Busam et al. | |
| 7,786,341 B2 | 8/2010 | Schneider et al. | |
| 2002/0120242 A1 * | 8/2002 | Tyrrell | A61L 15/40 604/364 |
| 2003/0105190 A1 | 6/2003 | Diehl et al. | |
| 2003/0148684 A1 | 8/2003 | Cramer et al. | |
| 2004/0102750 A1 | 5/2004 | Jameson | |
| 2004/0243078 A1 | 12/2004 | Guidotti et al. | |
| 2005/0008839 A1 | 1/2005 | Cramer et al. | |
| 2006/0135920 A1 | 6/2006 | Virgilio et al. | |
| 2007/0118087 A1 | 5/2007 | Flohr et al. | |
| 2008/0312617 A1 | 12/2008 | Hundorf et al. | |
| 2008/0312621 A1 | 12/2008 | Hundorf et al. | |
| 2008/0312622 A1 | 12/2008 | Hundorf et al. | |
| 2008/0312624 A1 | 12/2008 | Hundorf et al. | |
| 2009/0112173 A1 | 4/2009 | Bissah et al. | |
| 2009/0221978 A1 | 9/2009 | Gatto et al. | |
| 2011/0070277 A1 | 3/2011 | Vega et al. | |
| 2011/0250413 A1 | 10/2011 | Lu et al. | |
| 2011/0268932 A1 | 11/2011 | Catalan et al. | |
| 2011/0319846 A1 | 12/2011 | Rinnert et al. | |
| 2011/0319848 A1 | 12/2011 | McKieman et al. | |
| 2012/0123365 A1 | 5/2012 | Pan et al. | |
| 2012/0312491 A1 | 12/2012 | Jackels et al. | |
| 2012/0316526 A1 | 12/2012 | Rosati et al. | |
| 2012/0316527 A1 | 12/2012 | Rosati et al. | |
| 2012/0316528 A1 | 12/2012 | Kreuzer et al. | |
| 2012/0316529 A1 | 12/2012 | Kreuzer et al. | |
| 2012/0316530 A1 | 12/2012 | Armstrong-Ostle et al. | |
| 2012/0330262 A1 | 12/2012 | Lawson et al. | |
| 2012/0330263 A1 | 12/2012 | Lawson et al. | |
| 2014/0039434 A1 | 2/2014 | Xu et al. | |
| 2014/0039438 A1 | 2/2014 | Ferrer et al. | |
| 2014/0121621 A1 | 5/2014 | Kirby et al. | |
| 2014/0121623 A1 | 5/2014 | Biggs et al. | |
| 2014/0121624 A1 | 5/2014 | Kirby et al. | |
| 2014/0121625 A1 | 5/2014 | Kirby et al. | |
| 2014/0163501 A1 | 6/2014 | Ehrnsperger et al. | |
| 2014/0163504 A1 | 6/2014 | Bianchi et al. | |
| 2014/0303583 A1 | 10/2014 | Berrizbeitia et al. | |
| 2015/0065973 A1 | 3/2015 | Roe et al. | |
| 2015/0065976 A1 | 3/2015 | Roe et al. | |
| 2015/0282998 A1 * | 10/2015 | Arizti | A61F 13/15707 604/385.101 |
| 2015/0328063 A1 * | 11/2015 | Esping Ostlin | A61F 13/535 604/379 |
| 2016/0354260 A1 | 12/2016 | Roe | |
| 2019/0000688 A1 * | 1/2019 | Bianchi | A61F 13/551 |

FOREIGN PATENT DOCUMENTS

| | | |
|---|---|---|
| WO | WO9524173 | 9/1995 |
| WO | WO9917679 A2 | 4/1999 |
| WO | WO200071067 A1 | 11/2000 |

* cited by examiner

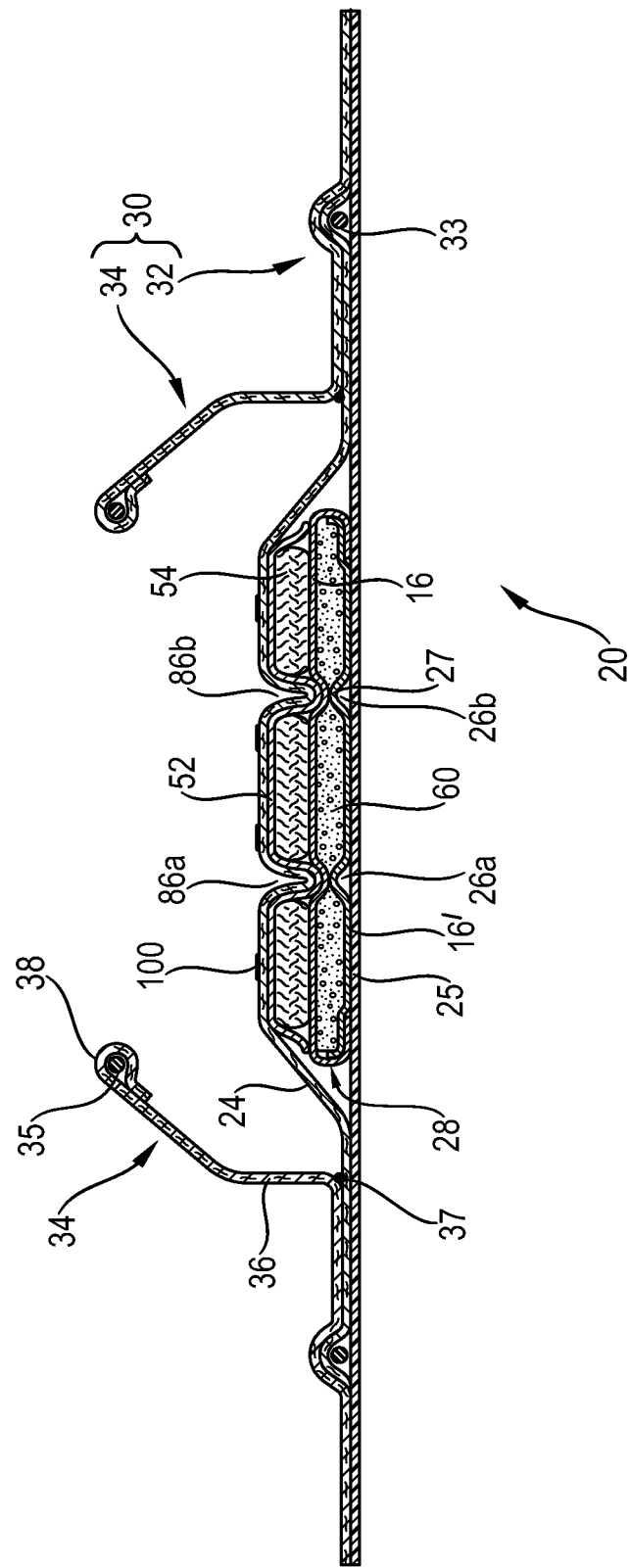

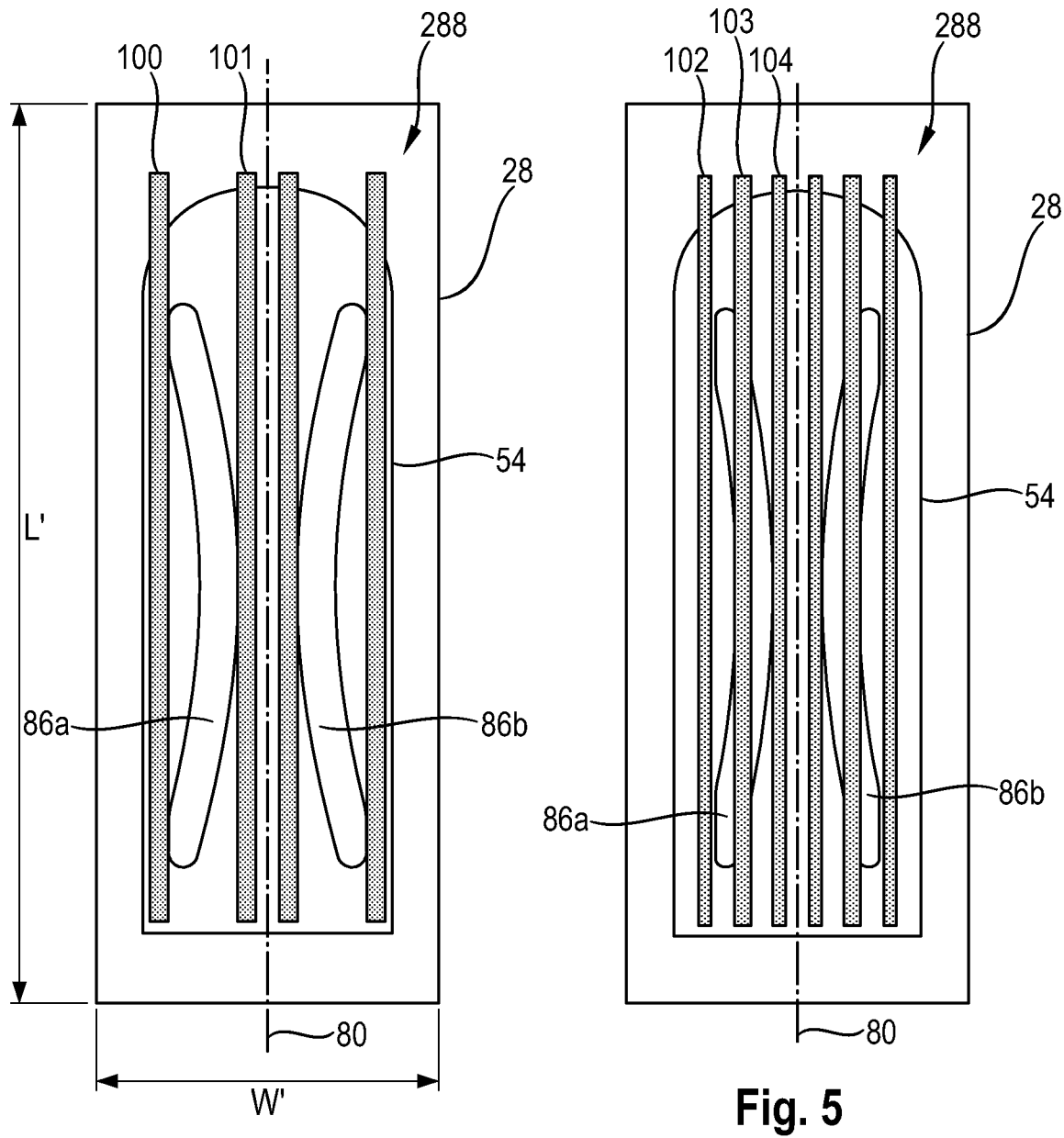

ABSORBENT ARTICLE WITH A LOTIONED TOPSHEET

FIELD OF THE INVENTION

The invention relates to personal hygiene absorbent articles that are placed in the crotch region of a wearer, such as baby diapers, training pants, feminine pads and adult incontinence products.

BACKGROUND OF THE INVENTION

Absorbent articles for personal hygiene are designed to absorb and contain body exudates, in particular large quantity of urine. These absorbent articles comprise a topsheet on the wearer-facing side that quickly acquires the fluid and feels soft on the wearer's skin, an absorbent core for retaining the fluid, and a backsheet on the garment-facing side for protecting the wearer's clothes.

One or more intermediate layers can be disposed between the topsheet and the absorbent core. These intermediate layers are designed to quickly acquire and/or distribute the fluid away from the topsheet and bring it effectively into the core. Such intermediate layers are sometimes individually called "wicking layer", "surge layer", "acquisition layer" or "distribution layer", and for multi-layer systems are sometimes collectively referred to as acquisition-distribution system (ADS) or liquid management system (LMS). These intermediate layers typically do not comprise superabsorbent material.

Absorbent articles having only one intermediate layer are commonly used. WO94/23761 (Payne) for example discloses an acquisition layer comprising an homogeneous composition of hydrophilic fibrous material comprising stiffened, twisted, and curled cellulose fibers and having a densified distribution zone. Other examples are found in U.S. Pat. Nos. 5,486,166 and 5,490,846 (Bishop). Articles having two intermediate layers or more, in particular an acquisition layer having a high capillarity which pulls the fluid quickly away from the topsheet and a distribution layer having a larger void area to distribute the fluid over a large surface over the core, are also known. For example WO2014/93323 (Bianchi et al.) discloses an absorbent article with a profiled acquisition-distribution system. Other exemplary references disclosing such intermediate layers are US2008/0312621 and US2008/0312622 (both Hundorf et al.), WO99/17679 (Everett et al.). Absorbent articles comprising channels in the absorbent core and overlapping channels in a liquid management system have been more recently disclosed in WO2015/31225, WO2015/31229, WO2015/31243 and WO2015/31256 (Roe et al.).

Some commercial articles are provided with a lotion on their topsheet. The lotion typically comprises hydrophobic skin-friendly ingredients as in a skin cream. Examples of lotion compositions are disclosed for example in WO2012/047986A1 (Pan et al.), WO2011/034867A1 (Vega et al.) and WO2009/102837A2 (Gatto et al.) to name a few. The lotion is partially transferred to the skin of the wearer during usage of the absorbent article, where it provides barrier properties against humidity and feces to reduce potential skin irritation. The lotion can be applied on the surface of the topsheet during manufacture by various application means, for example by a contact applicator that applies simultaneously a series of lotions stripes on the topsheet of the article in machine-direction. WO2006/066107 (Virgilio et al.) discloses a discontinuous lotion application pattern on the topsheet of an absorbent article.

While the known absorbent articles can have good overall properties, there is a continuous need to improve the skin protection properties of personal hygiene absorbent articles while maintaining the quality of the articles.

SUMMARY OF THE INVENTION

The present invention is directed to an absorbent article having a longitudinal axis extending in a longitudinal direction and a transversal axis extending in a transversal direction perpendicular to the longitudinal direction, wherein the absorbent article comprises:
  a fluid-permeable topsheet on the wearer-facing side of the article;
  a lotion on the topsheet wherein the lotion is applied on the topsheet according to a lotion application pattern, referred further therein as lotion pattern, and having a lotion pattern area;
  a fluid-impermeable backsheet on the garment-facing side of the article;
  an absorbent core between the topsheet and the backsheet, wherein the absorbent core comprises an absorbent material in a core wrap, the core wrap having a footprint as seen in the plane defined by the longitudinal axis and the transversal axis; and
  an intermediate layer between the topsheet and the absorbent core.

The intermediate layer will typically have fluid acquisition and/or distribution properties as is known in the art. The intermediate layer comprises at least one longitudinally-extending channel. The intermediate layer may in particular comprises a pair of such channels disposed symmetrically relative to the longitudinal axis. The channel(s) may be in particular area(s) substantially free of the intermediate layer material. The topsheet is depressed in the channel(s) so that the wearer-facing side of the article has at least one depression corresponding to the underlying channel(s) of the intermediate layer.

In a first aspect of the invention, the area of the channel(s) of the intermediate layer overlapping with the lotion pattern divided by the overall area of the channel(s) (herein "lotion-to-channel overlap") ranges from 0% to 20% of the area of the channel(s), or lower. The lotion pattern may advantageously comprise from 2 and up to 10 stripes of lotion that are oriented parallel to the longitudinal direction. Various advantageous optional features of the invention are described in the description below and claimed in the attached claims, for example the ratio of the lotion pattern area relative to the area of the footprint of the absorbent core may advantageously range from 5% to 25%.

The present invention addresses the problem of the lotion interacting with an underlying layer or component disposed under the intermediate layer, by minimizing the overlap between the lotion pattern and the channels in the intermediate layer. Such interaction may be negative for example in terms of the lotion reacting with an adhesive and weakening the adhesive bond.

BRIEF DESCRIPTION OF THE DRAWINGS

FIG. 3 shows a schematic transversal cross-section of the diaper of FIGS. 1-2.

FIG. 4 shows in a top view of the superposition of the lotion pattern comprising 4 stripes, the intermediate layer with channels and the absorbent core's footprint of the article of FIGS. 1-3.

FIG. 5 shows an alternative lotion pattern comprising 6 stripes superposed with the same layers as in FIG. 4.

DETAILED DESCRIPTION OF THE INVENTION

General Description of an Absorbent Article

Figure 1:
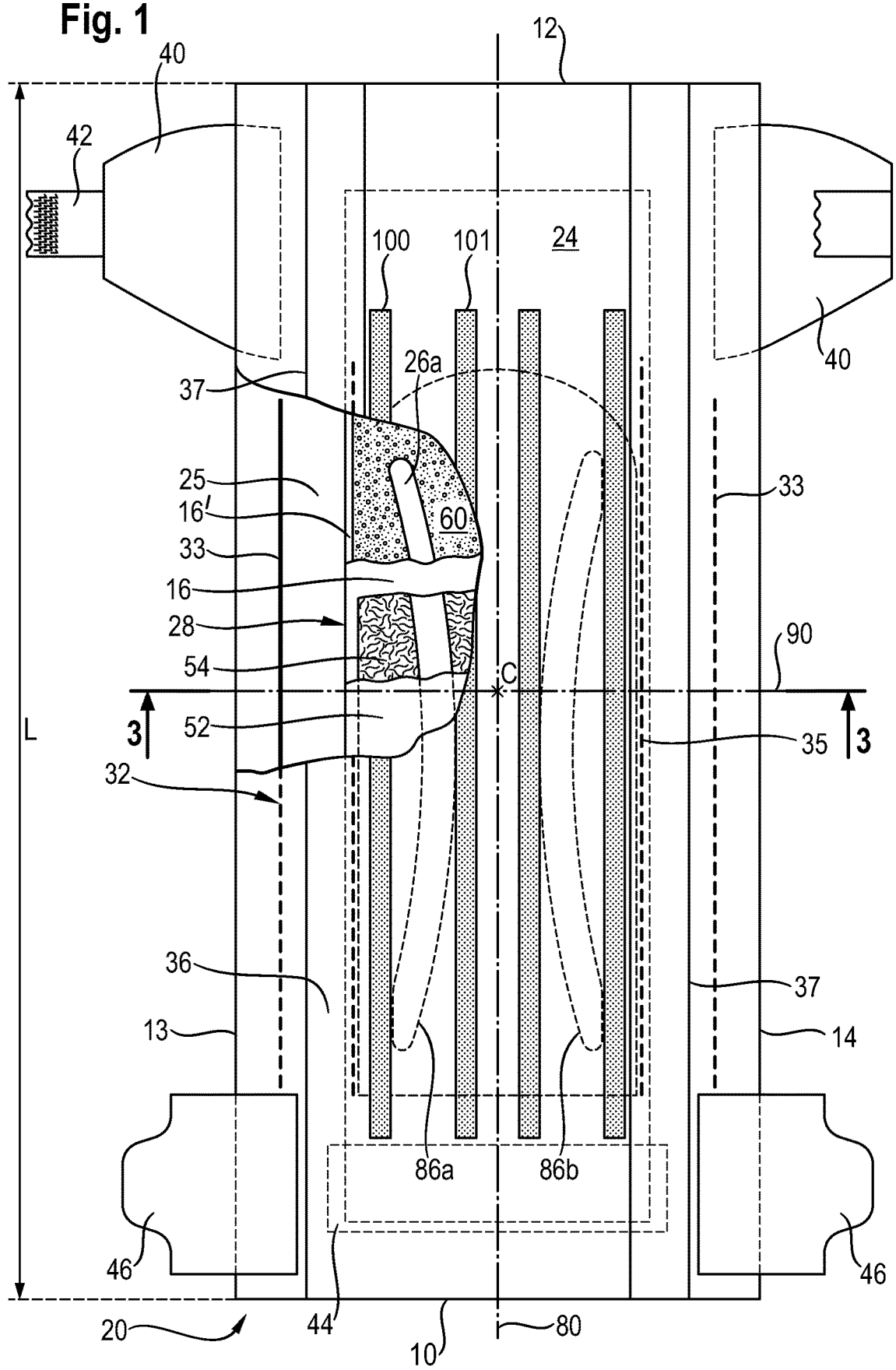
FIG. 1 is a top view of the wearer-facing side of an exemplary article of the invention in the form of a taped diaper which has been pulled flat, with some layers partially removed.
Figure 2:
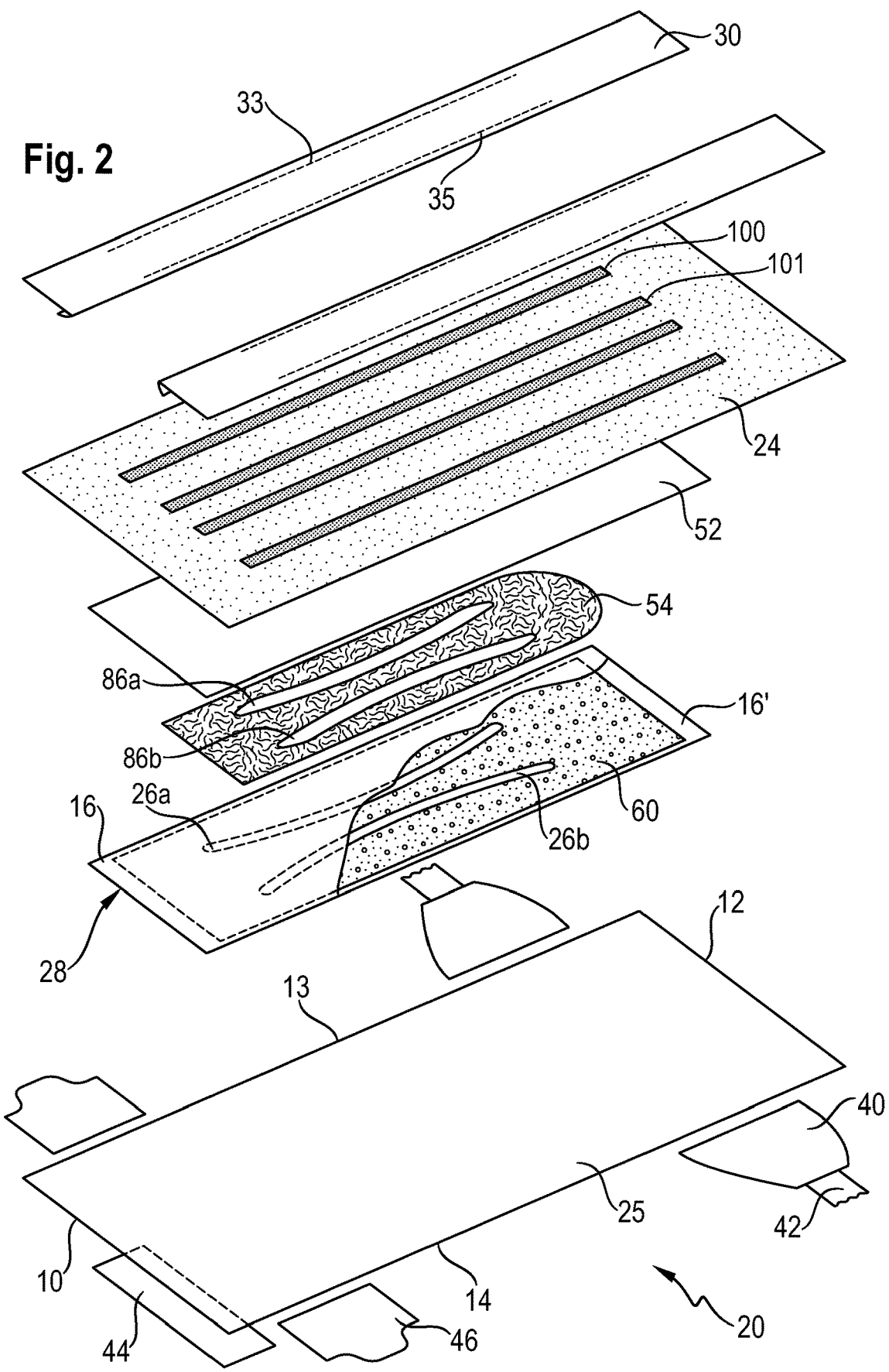
FIG. 2 shows a partial exploded view of the taped diaper of FIG. 1.
Figure 8:
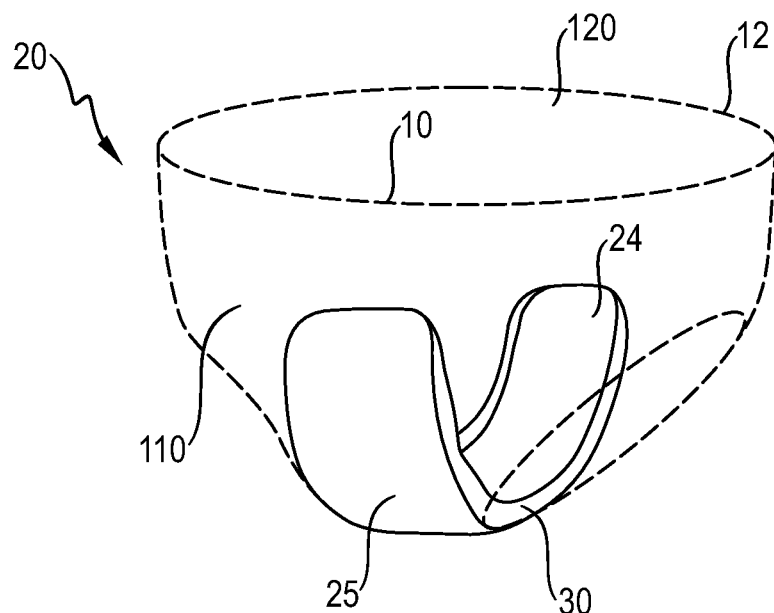
FIGS. 8-9 schematically show a pant type absorbent article that may also use the invention.
Figure 9:
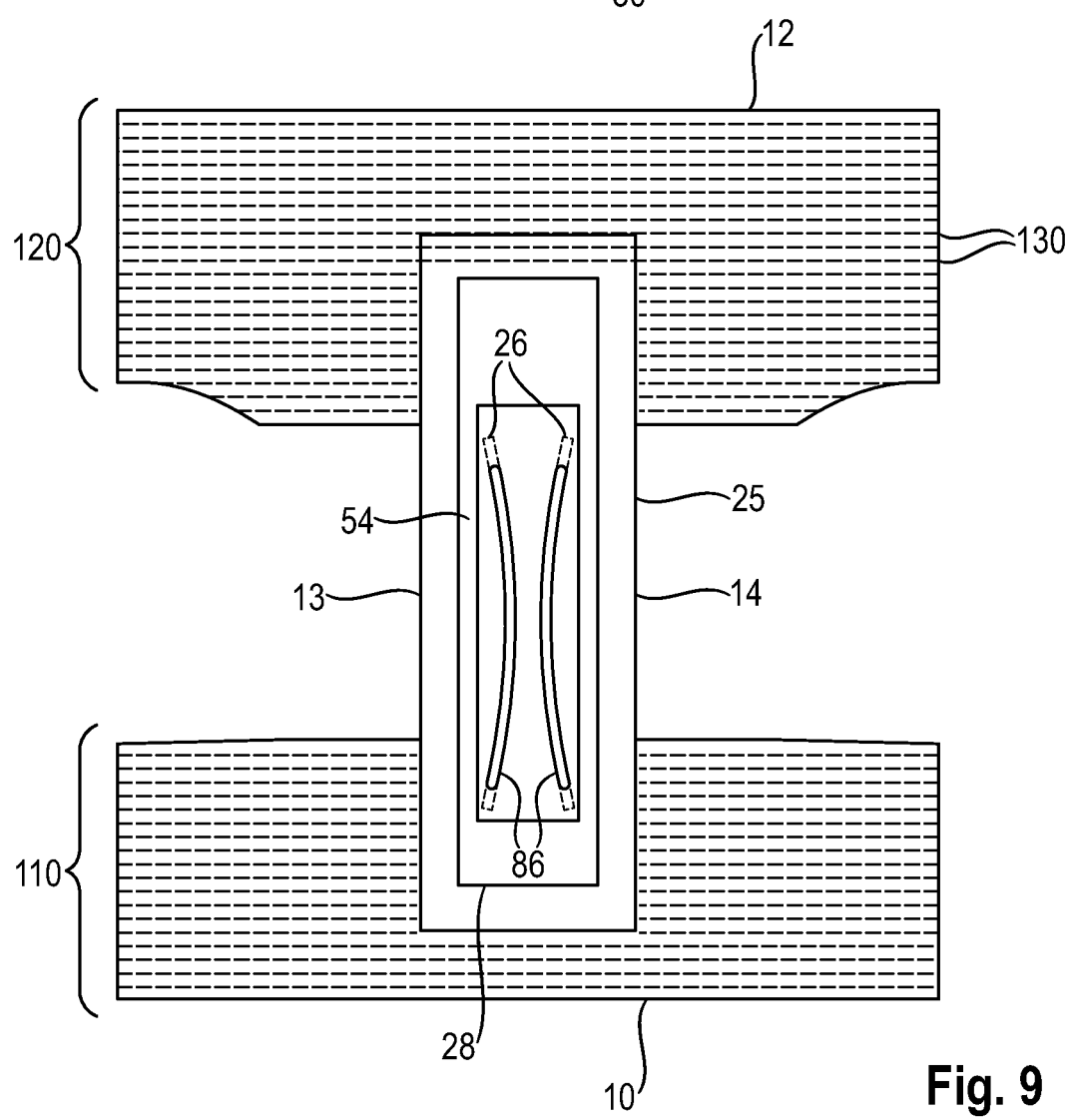

An exemplary absorbent article according to the invention in the form of a baby taped diaper 20 is represented in FIGS. 1-3. FIG. 1 is a top plan view of the wearer-facing side of an exemplary diaper in a flat-out state, with portions of the structure being cut-away to more clearly show the construction of the diaper. FIG. 2 is an exploded view showing the different layers of the diaper of FIG. 1. FIG. 3 is transversal cross-sectional view of the diaper 20 taken along line 2-2 in FIG. 1. This diaper 20 is shown for illustration purpose only, as the invention may be used for making a wide variety of diapers or other absorbent articles such as training pants, adult incontinence pants or feminine sanitary pads. FIGS. 8-9 for example schematically show a pant type absorbent article that may also use the invention. For ease of discussion, the absorbent cores and articles of the invention will be discussed with reference to the Figures and the numerals referred to in these Figures, however these are not intended to limit the scope of the claims unless specifically indicated.

As illustrated in FIG. 1, the absorbent article 20 comprises a front edge 10, a back edge 12, and two longitudinally-extending side (lateral) edges 13, 14. The front edge 10 is the edge of the article which is intended to be placed towards the front of the user when worn, and the back edge 12 is the opposite edge. The absorbent article is notionally divided by a longitudinal axis 80 extending along a longitudinal direction from the middle of the front edge to the middle of the back edge of the article and dividing the article in two substantially symmetrical halves relative to this axis, when viewing the article from the wearer-facing side in a flat out configuration, as exemplarily shown in FIG. 1. If some parts of the article are under tension due to elasticized components, the article may be typically flattened using clamps along the periphery of the article and/or a sticky surface, so that the article can be pulled taut so as to be substantially flat. Closed articles such as training pants or adult incontinent pants may be cut open along the side seams to apply them on a flat surface, as is known in the art. Unless otherwise indicated, dimensions and areas disclosed herein apply to the article in this flat-out configuration.

The article has a length L as measured along the longitudinal axis 80 (also called longitudinal centerline) from the back edge 12 to the front edge 10. The absorbent article can also be notionally divided by a transversal axis 90 (also called transversal centerline) into a front region and a back region of equal length measured on the longitudinal axis, when the article is in such a flat state. The transversal axis 90 is perpendicular to the longitudinal axis 80 and placed at half the length of the article. The intersection of the longitudinal axis 80 and the transversal axis 90 is defined herein as the centerpoint C of the article.

The absorbent article 20 comprises a liquid-permeable topsheet 24, a liquid-impermeable backsheet 25 and an absorbent core 28 between the topsheet and the backsheet. The absorbent core comprises an absorbent material 60 enclosed in a core wrap 16, 16'. An exemplary absorbent core 28 comprising a pair of channels 26 will be discussed further below in relation to FIGS. 6-7. The absorbent core has a footprint defined by its overall surface in a plane parallel to the longitudinal and transversal direction. The core footprint has typically the same shape as the core wrap, as viewed from above on a flat surface, as shown on FIG. 6 for example, which is referred to as the top surface 288 of the core in FIG. 7. The core footprint is typically rectangular as this is the simplest shape for making a core wrap. The footprint also includes the area of the core that do not comprise absorbent material, in particular the core's channel-forming areas 26 and the front edge 280 and back edge 282 of the core wrap where a front and/or end seals 280', 282' may be optionally present. The core's footprint is used to define the surface coverage of the lotion relative to the core footprint, as will be indicated below.

The absorbent article represented in the exemplary Figures also comprises two intermediate layers between the topsheet and the absorbent core: an acquisition layer 52 directly underneath the topsheet and a distribution layer 54 between the acquisition layer and the absorbent core 28. For clarity of the view of FIG. 1, the acquisition layer 52 is only partially shown (not shown in dotted lines), whereas the outline of the distribution layer 54 is shown completely including in dotted line. In the absorbent article illustrated herein, the distribution layer 54 is the intermediate layer having a pair of longitudinally-extending channels 86a,b. These channels are substantially free of distribution layer material. In the rest of the description, the intermediate layer comprising the channels will be referred to as the distribution layer 54, being understood that more generally the intermediate layer comprising the channels may be a distribution layer or any other kind of intermediate layers. The topsheet 24 is depressed in the channels so that the wearer-facing side of the article comprises a pair of depressions corresponding to the shape of the underlying channels. Advantageously, the topsheet is attached directly or indirectly through the channels to the underlying layer, which may typically be, as illustrated, the absorbent core 28 (more precisely the top layer 16 of the core wrap).

The wearer-facing side of the article is principally formed by the topsheet 24. The lotion pattern represented in FIG. 1 comprises four stripes of lotion 100, 101 applied parallel to the longitudinal direction. The longitudinal direction is typically the machine-direction (MD) in which the article is assembled, so that the lotion can be applied by intermittent application of a lotion using for example a contact applicator having 4 lotion outlets. In this example the outer pair of lotion stripes 100 is slightly wider than the inner pair of lotion stripes 101, but this is not critical, the stripes may also have the same width. The topsheet may advantageously comprise at least 2 and up to 10 stripes of lotion, as will be discussed further below. While not wishing to being bound by theory, it is believed that the depressions at the wearer-facing surface of the absorbent article increase the transfer rate of the lotion to the skin by helping to rub off the lotion onto the skin as the wearer of the article moves.

Other typical diaper components are represented in the Figures, such as elasticized gasketing cuffs 32 (also called outer cuffs), upstanding barrier leg cuffs 34 (inner cuffs), fastening tabs 42 and landing zone 44. For clarity of the drawings, only one elastic strand 33, 35 is shown for each cuff, but typically each cuff may comprise from 1 to 4 elastic strands. These further components will be discussed in more details further below. The absorbent article may also comprise other typical components, which are not represented in the Figures, such as a back elastic waist feature, a front elastic waist feature, transverse barrier cuffs, a wetness indicator that changes color when contacted with urine, etc.

The absorbent core represented comprises a pair of channel-forming areas 26 (not represented in dotted lines in FIG. 1 for clarity of the Figure). These channel-forming areas may be substantially free of absorbent material 60. The top side 280 of the core wrap may be bonded to the bottom side 290 of the core wrap through these channel-forming areas 26 by a channel bond 27, as illustrated on FIG. 7. When the absorbent material 60 around the channel-forming areas 26 absorbs a fluid and swells, the channel-forming areas of the core become more pronounced three-dimensional channels that are typically visible from the garment- and wearer-facing side of the article. The channels 86 of the intermediate layer according to the invention can advantageously cooperate with such channel-forming areas 26 present in an absorbent core 28, especially when the channel-forming areas 26 are at least partially superposed and parallel with the channels 86 of the distribution layer, as illustrated in the Figures. However this is not limiting of the invention, the absorbent core can also alternatively comprise channels without core wrap bonds, or the absorbent core may also be free of such channel-forming areas 26.

The topsheet 24, the backsheet 25, the absorbent core 28, the distribution layer 54 and acquisition layer 52 and the other article components may be assembled in a variety of well-known configurations, in particular by gluing, fusion, ultrasonic and/or pressure bonding as is known in the art. These bonds are typically not represented in the Figures to preserve readability of the Figures, but are present as is known in the art. The topsheet 24 can be attached directly or indirectly to an underlying layer through the channels 86 of the intermediate layer. If the channels are material free, as represented in the drawings, the topsheet may thus be bonded to the top side 280 of the absorbent core through the channels 86 of the distribution layer for example by adhesive bonding (gluing). Indirect bonding of the topsheet to an underlying layer may be for example provided when a first intermediate layer 52 not comprising channels is present between the topsheet and the intermediate layer 54 with the channels. In this case, and as represented in the Figures, the topsheet is attached indirectly to the absorbent core via this acquisition layer 52. The acquisition layer 52 may be a nonwoven layer, for example a latex bonded nonwoven. The distribution layer 54 may be a fibrous layer, for example a layer consisting of loosely bonded cross-linked cellulose fibers. However this is not limiting of the scope of the invention as many different types of intermediate layers are known in the art and may be used in the present invention. It is also possible that the channels in the intermediate layer are compressed areas of the intermediate layer, or areas of lower basis weight, rather the material free areas. In these cases the topsheet may be directly or indirectly bonded to these compressed or low basis weight channel areas and still form depressions on the wearer-facing side of the absorbent article.

The absorbent article is preferably thin. The article may for example have a caliper of from 1.0 mm to 8.0 mm, in particular from 1.5 mm to 6.0 mm, at the centerpoint C as measured using the Absorbent Article Caliper Test described below.

Lotion Pattern 100-105

The lotion is applied on the topsheet according to a pre-determined lotion application pattern, which is more simply referred herein as the lotion pattern. The lotion pattern covers a certain area of the topsheet referred herein as lotion pattern area. While not wishing to be bound by theory, it is believed that the lotion pattern area should be sufficiently large to allow for an efficient coverage and transfer of the lotion to the wearer's skin, but if the lotion pattern area is too large, this can cause a negative "shield" effect in terms of fluid absorption through the topsheet. This is because the lotion is typically hydrophobic and thus may hinder fluid absorption if it covers an area which is too large. The lotion pattern area may thus advantageously represent from 5% to 25% of the footprint of the absorbent core. Having a coverage lower than 5% may be insufficient to provide an efficient lotion deposition over a sufficiently large area of the wearer's buttocks, while having a lotion pattern area higher than 25% may hinder the overall fluid acquisition. The lotion pattern area to the absorbent core's footprint ratio may more particularly range from 10% to 20%, or 12% to 18%.

The lotion pattern is furthermore advantageously circumscribed within the absorbent core's footprint, in other words the lotion pattern advantageously does not extend beyond the transversal edges 284, 286 and longitudinal edges 280, 282 of the absorbent core when the article is viewed from the top as in FIG. 1. The lotion pattern may be furthermore circumscribed to the absorbent material deposition area of the core which comprises the absorbent material 60, excluding the front end and back end 280, 282 of the core wrap where a seal 280', 280' may be present. The footprint of the absorbent core is typically the area formed by the top side 288 of the core wrap, and its area can be directly read from the manufacturer specification of the absorbent core. If the specification is not directly available (e.g. because a third party's product is analyzed) the core footprint's area can be measured directly on the absorbent core 28. The lotion pattern area can be similarly directly read from the manufacturer's specification, or if these are not available can be measured directly on the topsheet of the article. Lotion pattern are usually easily recognizable on the topsheet due the visual contrast between the topsheet's lotion-covered areas and the lotion-free areas. Lotions can also be slightly sticky due to some of their ingredients so that a fine powder like talc may be used to highlight the lotion pattern of an unknown product. The lotion pattern area can thus be measured experimentally using a ruler or by taking a digital picture which is then treated using any standard picture analysis software.

The lotion pattern is advantageously applied as a plurality of longitudinally-oriented stripes (also called slots) which are separated from one another in the transversal direction. By longitudinally-oriented it is meant parallel to the longitudinal direction. Such lotion pattern can be applied on the topsheet using a lotion applicator placed on the manufacturing line and having a series of lotion outlets, as is known in the art. The lotion applicator can be switched on and off extremely rapidly to obtain the desired length and placement of the stripes on the topsheet of the individual articles. The width of the stripes is defined by the width of the outlets. The stripes may all have the same width or the stripes may have different widths. The stripes may typically have all the same length in the longitudinal direction, but it is not excluded that the stripes may have different lengths. The lotion pattern is typically symmetrically disposed relative to the longitudinal axis.

The lotion pattern of the invention advantageously comprises at least 2 and up to 10 longitudinally-oriented stripes. Each of these stripes is separated from one another in the transversal direction. The lotion pattern may in particular comprise from 3 to 9 stripes of lotion, more particularly from 4 to 8 stripes, that is 3, 4, 5, 6, 7, 8 or 9 stripes. Each stripe may be typically continuous as represented in the Figures, but it is not excluded that one or more stripe may be discontinuous, for example having an interruption towards the center of the topsheet. Because the lotion is typically hydrophobic, it may be desired to keep this central area free of lotion but this is not critical. The basis weight at which the lotion is applied is typically the same for every stripes. Typical basis weight for the lotion deposited on the topsheet may for example range from 8 gsm to 20 gsm, in particular 10 gsm to 18 gsm.

While not wishing to be bound by theory, it is believed that it is advantageous to have at least two lotion stripes, so that at least one lotion stripe is on each side of the longitudinal axis for a more consistent lotion deposition on each buttock of the wearer. Furthermore having a single central stripe means that the stripe would be relatively large, which may be negative in terms of fluid running-off as the lotion composition typically comprises hydrophobic ingredients with liquid barrier properties. It is also believed that having too many stripes would require using too small orifices for the lotion applicator. Because the lotion is applied in a molten, relatively viscous state, having small width stripes require applying the lotion at higher pressure. This may be detrimental for the correct application of the lotion, in particular the lotion may be forced by the high pressure through the topsheet and thus become less available on the wearer facing-side. The width of the stripes may accordingly range from 1 mm to 20 mm for at least some of the stripes and advantageously for all the stripes, in particular from 2 mm to 10 mm, or from 2 mm to 8 mm.

Two exemplary stripe patterns are illustrated in FIG. 4 and FIG. 5. For clarity, these Figures only show the lotion pattern 100-105, the intermediate layer 54 having the channels 86 and absorbent core's footprint 280. The topsheet 24 on which the lotion is applied, an optional first intermediate layer 52 and the channel-forming areas 26 of the core are omitted for clarity.

Lotion Pattern Example 1

The lotion pattern of FIG. 4 comprises four lotion stripes of equal length and symmetrically disposed relative to the longitudinal axis. The inner stripes 101 are slightly narrower than the outer stripes 100. While the Figures are schematic, exemplary dimensions that can be used for this pattern e.g. for a size 4 diapers, is as follows:
    Absorbent core length (L'): 390 mm
    Absorbent core Width (W'): 120 mm
    Core footprint area: 468 cm2
    Length of the stripes: 320 mm
    Width of the inner stripes: 4.5 mm
    Inner Stripes to CL Distance: 4 mm
    Width of the outer stripes: 5 mm
    Outer Stripes to CL distance: 26 mm
    Overall area of the lotion pattern: 60.8 cm2
    Lotion to core's footprint area ratio: 13.0%
The distance to CL (centerline 80) is reported as from the inner edge of each stripe. The lotion in this example may be applied at a basis weight of 15 gsm for each stripe, with an overall add-on level of about 92 mg of lotion for the diaper. This lotion pattern may be of course used on other diaper sizes, by adapting the dimensions to the size of the diaper's chassis considered. The layer 54 has a length of 289 mm, a width of 80 mm, and the channels 86 have a length of 173 mm and a width of 8 mm.

This first lotion pattern minimizes the overlap of the lotion pattern on the topsheet with the underlying channels 86a,b in the intermediate layer to an overlap value of below 5%. While not wishing to be bound by theory, it is believed that if the lotion composition overlaps with the channels 86, it may in some instances migrate from the surface of the topsheet through the channels onto the underlying layer. The underlying layer may be the absorbent core 28. If the topsheet is attached directly or indirectly through the channels 86 to the underlying layer by an adhesive, the lotion composition and the adhesive may over time and/or especially at higher temperature (for example in summer or in hot countries) negatively interact. This interaction such as the adhesive dissolving in the lotion, may ultimately lead to a weaker bond.

Thus, it is advantageous that the lotion pattern has a limited overlap with the channels of the intermediate layer. In particular, the area of the channels of the intermediate layer overlapping (in the vertical direction) with the lotion pattern is no more than 20% of the total area of the channels ("lotion-to-channel overlap ratio"). The lotion-to-channel overlap ratio is advantageously even lower, in particular no more than 15%, or no more than 10%, or no more than 5% (of the total area of the channels). The lotion-to-channel overlap ratio may be for example from 0% to 20%, or from 1% to 15%, or from 2% to 10% or from and to any sub-ranges obtained by combining any of the upper and lower values of these ranges. The lotion pattern example 1 (with four stripes) is designed to minimize the overlap, having a lotion-to-channel overlap ratio value of from 0% to 5%. The lotion-to-channel overlap ratio is expressed in percentage and can be calculated or measured as indicated herein below in the test procedure section.

Comparative Lotion Pattern Example 2

A second lotion pattern outside the invention is illustrated in FIG. 5 and comprises 6 stripes of lotion (an outer pair 104, a central pair 103 and an outside pair 102) as comparison. The dimensions are indicated as follows in the context of a size 4 baby diaper, but this lotion pattern may be of course used on other diaper sizes, by adapting the dimensions to the size of the diaper's chassis considered.
    Absorbent core length (L'): 390 mm
    Absorbent core Width (W'): 120 mm
    Core footprint area: 468 cm2
    Length of the stripes: 320 mm
    Width of the inner stripes: 3 mm
    Inner Stripes to CL Distance: 4 mm
    Width of the central stripes: 6 mm
    Central Stripes to CL Distance: 14.5 mm
    Width of the outer stripes: 3 mm
    Outer Stripes to CL distance: 28 mm
    Overall area of the lotion pattern: 76.8 cm2
    Lotion to core's footprint area ratio: 16.4%
The distance to CL (centerline 80) is reported as from the inner edge of each stripe. The layer 54 has a length of 289 mm, a width of 80 mm, and the channels 86 have a length of 173 mm and a width of 8 mm. The lotion in this example may be applied at a basis weight of 12 gsm, with an overall add-on level of 92 mg for the diaper. The lotion pattern example 2 (with six stripes) has a lotion-to-channel overlap ratio of about 24%.

Lotion Composition

The invention can be used with any known lotion compositions. Advantageously the lotion is applied heated in a liquid or semi-liquid form by slot coating technology as indicated before, wherein the lotion immediately solidifies on the topsheet after being applied, as is known in the art. Lotion composition typically comprises hydrophobic components such as liquid paraffin, petrolatum, fatty esters, fatty alcohols (e.g. stearyl alcohol), etc. different examples of composition patents have been indicated in the background section above. The lotion is applied according to a defined basis weight, which is the quantity of lotion per unit of area (of the lotion pattern). Typically the basis weight may be the same for all stripes but it is not excluded that they may also differ. The overall add-on level per article can be varied depending of the type of executions considered, as is known in the art.

Experimental: Channel Bond Strength Over Time

Diapers having the general construction as shown in FIGS. 1-3 and thus comprising channel-forming areas in the absorbent core and matching channels in the intermediate distribution layer were made. The top side of the core wrap is adhesively attached to the bottom side of the core wrap in the channel-forming areas. Half of the diapers were applied with the lotion pattern of example 1 (lotion-to-channel overlap ratio value of up to 5%) and the other half of the diapers with the lotion pattern of example 2 (lotion-to-channel overlap ratio of about 24%).

The strength of the adhesive bonds in the channel-forming areas were measured several weeks after application of the lotion ("fresh"). The diapers were then submitted to accelerated aging (40° C./75% RH) for several months, and the adhesive bond strength was measured after 1 month, 2 months, 3 months and finally 6 months of accelerated ageing. The bond strength in N is the maximum force measured required to peel the top side of the core wrap from the bottom side of the core wrap in the cross direction of the sample. The average values recorded in N for the channel-forming areas on the Operator Side (Op, where the operator can access the machine) and Driver Side (Dr, the other side of the converting line) are recorded as follows. 10 measurements were made for each average value. The percentage of the bonds measured having a strength of more than 0.3N, defined herein as the limit where a bond can be considered to be effective, is also recorded in the table below.

|  | Example 1: 4 stripes pattern (max 5% overlap) | Comparative Example 2: 6 stripes pattern (24% overlap) |
| --- | --- | --- |
| Fresh Average Strength (N) Dr/Op Side | 0.91/0.72 | 0.84/0.69 |
| % Presence (>0.3 N force) | 95% | 100% |
| 1 m Ageing Average Strength (N) Dr/Op Side | 0.69/0.55 | 0.64/0.54 |
| % Presence (>0.3 N force) | 95% | 90% |
| 2 m Acc Ageing Average Strength (N) Dr/Op Side | 0.61/0.43 | 0.54/0.31 |
| % Presence (>0.3 N force) | 90% | 65% |
| 3 m Acc Ageing Average Strength (N) Dr/Op Side | 0.58/0.42 | 0.53/0.37 |
| % Presence (>0.3 N force) | 85% | 80% |
| 6 m Acc Ageing Average Strength (N) Dr/Op Side | 0.60/0.40 | 0.51/0.30 |
| % Presence (>0.3 N force) | 80% | 55% |

Comparing the data statistically, the bond strength is significantly higher for the channel-forming area on the Operator Side (at 2, 3 and 6 month) on a 95% confidence level for the diapers according to example 1 relative to comparative example 2, and at 80% confidence of the Driver Side. In conclusion, it was found that already after one month of accelerated ageing, the inventive lotion application pattern with 4 lotion stripes having a minimum overlap with the channels in the distribution layer delivers a significant improvement of the strength of the adhesively bonded channels-forming areas of the underlying absorbent core.

Experimental: Lotion Deposition

Different absorbent articles were tested to measure the amount of lotion deposition of different baby diapers in real usage conditions after 4 hours and after 24 hours of wear time. The 4 hours measurements were made using a single diaper, while for the 24 hours measurements diapers having the same construction were changed by the caregivers according to their usual usage practice. The different diapers were applied with a lotion pattern including 4 stripes or 6 stripes of lotion, as illustrated in FIG. 4 and FIG. 5 respectively. The babies wearing the diaper did not wear lotioned diapers for at least 4 days before the test and were bathed immediately before the test to remove any previously applied lotion on their skin. Two large medical sticky square tapes (ca. 20 cm2 each) were gently stuck in the middle of each buttock. The tapes simulate the skin of the wearer and can pick-up the lotion by transfer from the topsheet of the diaper. One of the tape was collected after 4 hours of wear of the first diaper, and the other after 24 hours. The tapes are analyzed to measure the amount of lotion deposited on each tape.

Four different diaper variants were tested. The first diaper variant comprised a pair of channels in its distribution layer (cross-linked cellulose) and had a 6 stripes pattern as indicated the example 2 above. The second diaper variant was constructed as the first diaper variant with the difference that the four stripes pattern as discussed above in example 1 was used. The third diaper variant did not comprise channels in the distribution layer but was otherwise constructed like the first diaper variant. The fourth diaper variant was constructed as the second diaper variant but had a lower amount of lotion (lotion basis weight of 12 gsm instead of 15 gsm). This and the results obtained are summarized below:

| Hour 4 | | | | | | | |
|---|---|---|---|---|---|---|---|
| Test Product | Number of stripes | Channels in the distribution layer | Lotion basis weight (gsm) | Add-on level (mg) | Number of Subjects | Lotion Transfer Mean (μg/cm2) | Standard Error (μg/cm2) | Lotion Transfer ≥5000 μg per Tape* |
| Diaper variant 1 | 6 | Yes | 12 | 92 | 13 | 101.3 | 12.67 | 0 |
| Diaper variant 2 | 4 | Yes | 15 | 92 | 11 | 96.9 | 13.48 | 0 |
| Diaper variant 3 | 6 | No | 12 | 92 | 13 | 78.3 | 12.68 | 0 |
| Diaper variant 4 | 4 | Yes | 12 | 74 | 12 | 61.8 | 13.05 | 0 |

As can be seen, after 4 hours of wear, the lotion transfer for the diaper variant 1 and diaper variant 2 was significantly greater than for diaper variant 3. This shows that the presence of the channels in the distribution layer increased the deposition rate of the lotion relative to the same diaper having no channels in the distribution layer (diaper variant 3). Another significant factor for the deposition rate is the overall amount of lotion, diapers having a lower lotion add-on level (diaper variant 4) had a lower lotion transfer at 4 hours than a similar diaper having more lotion (diaper variant 2).

After 24 hours on the other hand, the lotion transferred onto the test tapes was not significantly different between the 4 diapers, as can be seen in the summary table below.

| Maximum force (N) | | |
|---|---|---|
| | Diaper variant 1 (with channels in intermediate layer) | Diaper variant 3 (no channels in intermediate layer) |
| Sample 1 | 0.78 | 3.37 |
| Sample 2 | 0.84 | 3.66 |
| Sample 3 | 1.06 | 2.50 |
| Sample 4 | 0.74 | 2.97 |
| Sample 5 | 0.97 | 3.30 |
| Average Maximum Force | 0.88 | 3.16 |

| Hour 24 | | | | | | | |
|---|---|---|---|---|---|---|---|
| Test Product | Number of stripes | Channels in the distribution layer | Lotion basis weight (gsm) | Add-on level (mg) | Number of Subjects | Lotion Transfer Mean (μg/cm2) | Standard Error (μg/cm2) | Lotion Transfer ≥5000 μg per Tape1 |
| Diaper variant 1: | 6 | Yes | 12 | 92 | 13 | 220.0 | 13.70 | 6 |
| Diaper variant 2: | 4 | Yes | 15 | 92 | 10 | 215.1 | 15.48 | 3 |
| Diaper variant 3: | 6 | No | 12 | 92 | 13 | 216.5 | 13.70 | 5 |
| Diaper variant 4 | 4 | Yes | 12 | 74 | 12 | 207.1 | 14.22 | 3 |

1) the analytical method sensibility loses precision for lotion transfer at or above 5000 μg per tape. In these cases the lotion transfer value per tape was changed to 5000 μg.

Lateral Compression Force Measurements

While not wishing to be bound by theory, it is believed that articles comprising longitudinally-extending channels in the intermediate layer are more flexible in the transversal direction than similar articles without these channels. It is believed that an increased flexibility may help improve the transfer of the lotion in the initial hours. The Lateral Compression Force Measurement Method described below was performed on five diapers according to diaper variant 1 (which is according to the construction of the diaper schematically represented in the Figures and comprise channels in the intermediate layer). The same measurements were repeated on five diapers according to diaper variant 3, which has no channels in the intermediate layer but are otherwise identical to the diaper variant 1. The results were as follows:

While not wishing to be bound by theory, it is thus believed that it is advantageous that the absorbent articles of the invention have a relatively low lateral compression force to improve the initial transfer of the user. In an aspect of the present invention, the average lateral compression force for a given article's construction (as measured by the test described hereinbelow) may thus be less than 3.0 N, in particular 2.5 N or less, 2.0 N or less, 1.5N or less, 1.0 N or less. The force may for example range from 0.1N to 2.5N. The lotion pattern is not believed to change the lateral compression force value, which will more likely depend on the construction and material of the diaper.

Channels 86 in the Intermediate Layer 54

The absorbent article comprises at least one intermediate layer between the topsheet 24 and the absorbent core 28 comprising channels 86. In the example of the Figures, the distribution layer 54 is the intermediate layer comprising the channels. This intermediate layer comprises at least one longitudinally-extending channel, and preferably at least a pair of such channels 86 comprising a first longitudinally-extending channel 86*a* on one side of the longitudinal axis 80, and a second longitudinally-extending channel 86*b* on the other side of the longitudinal axis. In the description, the plural form "channels" will be used for simplicity to mean "one or more channels" and in particular "a pair of channels" unless explicitly indicated otherwise.

Channels are areas within the intermediate layer that are depressed relative to the rest of the intermediate layer. The channels are advantageously substantially free of the intermediate layer's material, for example from distribution layer's material, as represented in the Figures. By "substantially free" it is mean that there is no such material present in the channels, with of course the possible exception of involuntary minor material deposits (fibers) which is difficult to avoid during the manufacturing process. Alternatively, channels may also be formed by areas having a lower basis weight than the rest of the layer, or channels may also be compressed areas of the intermediate layer.

The channels may be straight or curved or partially straight and partially curved, when considered from above with the article flattened up as on FIGS. 4-5. In particular, the channels may be concave (inwardly curved) towards the longitudinal axis 80 as illustrated in FIG. 1. Alternatively, it is not excluded that the channels may be partially or entirely straight, and in particular longitudinally-oriented (that is parallel to the longitudinal axis 80), or convexly curved in the other direction. The channels are typically disposed as one or more symmetrical pair(s) relative to the longitudinal axis, and are spaced apart from one another over their whole longitudinal dimension. The minimum distance between a pair of channels may be for example at least 5 mm, or at least 10 mm, or at least 16 mm. It is however not excluded that the channels may be joined together, for example at their back extremities to form a fecal waste pocket. The minimum distance between two channels may thus be of at least 10 mm as measured along the longitudinal axis 90. Furthermore, in order to reduce the risk of fluid leakages, the channels advantageously do not extend up to any of the edges of the distribution layer, and are therefore surrounded by and fully encompassed within the distribution layer. The minimum distance between a channel and the closest edge of the distribution layer may be at least 5 mm. Distribution layer with at least two material-free channels have been also disclosed for example in WO2015/31225 (Roe et al.).

The channels 86 are longitudinally-extending, meaning that they extend at least as much in the longitudinal direction 80 than in the transversal direction 90, and typically at least twice as much in the longitudinal direction than in the transverse direction (as measured after projection on the respective axis). The channels may for example have a length projected on the longitudinal axis 80 of the article that is at least 15% of the length L of the absorbent article, in particular from 20% to 80% of the length L. The channels may also have a width along at least part of their length which is at least 2 mm, or at least 3 mm or at least 4 mm, up to for example 20 mm, or 16 mm or 12 mm. The width of each channel may be constant through substantially the whole length of the channels or may vary along its length.

Distribution Layer 54

The intermediate layer comprising the channels may be a distribution layer, so that the description below also applies generally for describing an intermediate layer according to the invention. This is however not limiting as the invention is not limited to the intermediate layer being a distribution layer. The function of a distribution layer is to spread an insulting fluid liquid over a larger surface within the article so that the absorbent capacity of the core can be more efficiently used. The distribution layer, or more generally any intermediate layer comprising the channels, may be smaller in surface than the absorbent core's footprint and does not extend beyond the edges of the core's footprint. The distribution layer is typically made of a fibrous material, which may be based on synthetic or cellulosic fibers.

The distribution (or intermediate) layer may thus be a fibrous layer which has an average basis weight of at least 50 g/m2, in particular from 50 g/m2 to 300 g/m2, and advantageously at least at least 100 g/m2. The average basis weight is calculated by dividing the weight amount of the fibers by the area of the intermediate layer where the fibers are present, excluding the areas of the channel(s) in the intermediate layer. The distribution/intermediate layer may have a relatively low density. The density of the layer may vary depending on the compression of the article, but may typically range from 0.03 g/cm3 to 0.25 g/cm3, in particular from 0.05 g/cm3 to 0.15 g/cm3, measured at 0.30 psi (2.07 kPa). The density of the distribution layer is measured at the centerpoint C of the article for this purpose.

The fibrous material may be manufactured by air-laying the fibers on a drum comprising several molds each having the required depth profile for the desired fibrous material configuration. The formed distribution layer can then be directly un-molded onto another component of the article such as a nonwoven carrier layer and then integrated with the rest of the article. There may be other layers between the distribution layer and any of the topsheet and the absorbent core, for example an acquisition layer 52. When a nonwoven acquisition layer is present in the article, the distribution/intermediate layer 54 may be for example deposited on this acquisition layer, the two layers being further joined to absorbent core and the rest of the article, as is known in the art.

The general outline of the distribution/intermediate layer as seen from above may be generally rectangular, as is typical in the art, but may be also shaped (that is non-rectangular), for example having a bullet shape as illustrated on FIG. 1 with a back edge that is rounded. The different configurations can be used to maximize the efficiency of the distribution layer for different applications. The distribution layer may be profiled in the longitudinal direction (see e.g. WO2014/93323, Bianchi et al.). A particularly preferred distribution material comprises or consists of cross-linked cellulose fibers, as will be detailed further below, but other typical distribution materials can also be used.

The distribution/intermediate layer is typically a fibrous layer. The distribution/intermediate layer may be a nonwoven material comprising fibers that are bonded to another so that the layer has a strong integrity and may be manipulated independently of a substrate. Alternatively, the distribution layer may be another type of fibrous layer, in particular the distribution layer may comprise or consist of loose fibers with no or weak intra-fiber bonds, the fibers being deposited on a supporting substrate at varying basis weight to form a profiled distribution. A typical example of distribution/intermediate material comprises or consists of cross-linked cellulose fibers. The distribution/intermediate layer may for example comprise at least 50% by weight of cross-linked cellulose fibers. The cross-linked cellulosic fibers may be crimped, twisted, or curled, or a combination thereof including crimped, twisted, and curled. This type of material has been used in the past in disposable diapers as part of an acquisition system, for example US 2008/0312622 A1 (Hundorf). The cross-linked cellulosic fibers provide higher resilience and therefore higher resistance against the compression in the product packaging or in use conditions, e.g. under baby weight.

Exemplary chemically cross-linked cellulosic fibers suitable for a distribution layer are disclosed in U.S. Pat. Nos. 5,549,791, 5,137,537, WO95/34329 or US2007/118087. The distribution layer comprising cross-linked cellulose fibers may comprise other fibers, but this layer may comprise at least 50%, or 60%, or 70%, or 80%, or 90% or even up to 100%, by weight of the layer, of cross-linked cellulose fibers (including the cross-linking agents). While the distribution material may be comprised of cellulose fibers, in particular cross-linked cellulose fibers, other materials are possible, in particular any fibrous material having a Water Retention Value of from 2 to 60, as measured by Water Retention Value Procedure described herein.

General Description of an Absorbent Core

Figure 6:
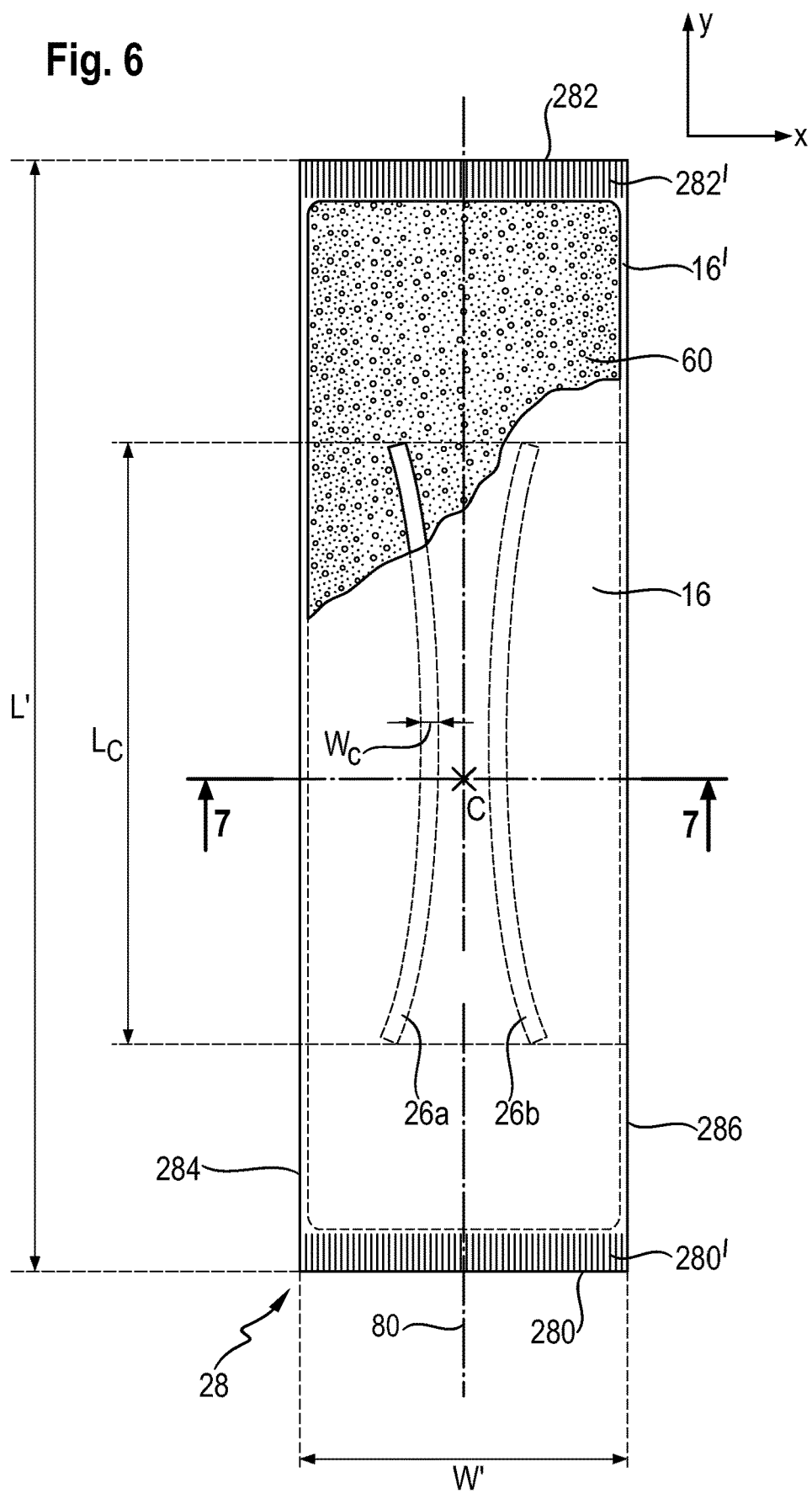
FIG. 6 is a top view of an exemplary absorbent core comprising two curved channel-forming areas, with the top layer of the core wrap partially removed, shown in isolation.
Figure 7:
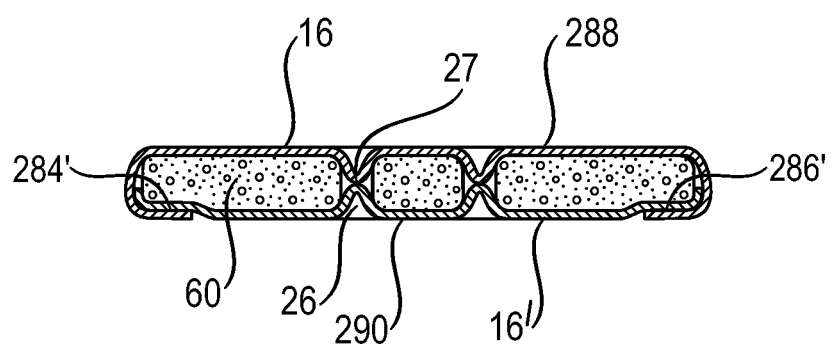
FIG. 7 is a schematic transversal cross-section of the core of FIG. 6.

An exemplary absorbent core 28 taken in isolation is illustrated on FIGS. 6-7. As used herein, the term "absorbent core" or "core" refers to a component of an absorbent article which comprises an absorbent material contained in a core wrap. As used herein, the term "absorbent core" does not include the topsheet, the backsheet or a distribution/acquisition layer. The absorbent core has typically the most absorbent capacity of all the components of the absorbent article, and comprises all or at least the majority of superabsorbent polymer (SAP) in the article. The core typically thus consists essentially of, or consists of, the core wrap, the absorbent material and optionally adhesives. The absorbent material may consist of SAP in particulate form as exemplified in the present description but it is not excluded that other type of absorbent material may be used. The terms "absorbent core" and "core" are herein used interchangeably.

The absorbent core may be substantially planar so that it can be laid flat on a surface. The absorbent core may also be typically thin and conformable, so that it can also be laid on a curved surface for example a drum during its making process or stored as a continuous roll of stock material before being converted into an absorbent article. FIGS. 6-7 schematically show an absorbent core that can be used in the invention. Such a core is for example disclosed in WO2012/170778 (Rosati et al.) that discloses absorbent structures that comprise superabsorbent polymers, optionally a cellulosic material, and at least a pair of substantially longitudinally-extending channels (see also WO2012/170779, WO2012/170781 and WO2012/170808). The core wrap can be adhesively bonded through the channels to form a channel bond. The integrity of the channel bonds may be at least partially maintained in wet state.

The absorbent cores used in the invention may comprise the same basic features as the absorbent core represented on FIG. 6. For ease of discussion, this exemplary absorbent core is represented in a flat state and extending in a plane along a transversal direction and a longitudinal direction, as in FIG. 1. Unless otherwise indicated, dimensions and areas disclosed herein apply to the core in this flat-out configuration. The same applies to an absorbent article, as exemplarily represented in FIG. 1, in which the core is integrated.

The intermediate layer with channels advantageously cooperate with the underlying absorbent core to provide improved performance in terms of fluid handling and/or wearing comfort. The absorbent core 28 may in particular advantageously comprise at least one, and as represented at least two longitudinally-extending areas that are substantially free of absorbent material, which are herein referred as channel-forming areas 26a, 26b. The channel-forming areas 26 may be longer or shorter than the channels 86 of the distribution layer, but advantageously the channel-forming areas of the core correspond at least along a portion of their length to the channels in the distribution layer. In this way, the fluid can be directly transferred vertically via the channels of the intermediate layer to the channel-forming areas of the core.

The footprint of the absorbent core is typically defined by the core wrap. The core wrap may comprise two individual substrates 16, 16' as illustrated in the Figures, but it is also common and possible to have a single substrate forming the core wrap. The absorbent core typically comprises a front edge 280, a back edge 282 and two longitudinally-extending side edges 284, 286 joining the front edge and the back edge. The front edge is the edge of the core placed towards the front edge 10 of the absorbent article. Typically the absorbent material 60 of the core may be advantageously distributed in somewhat higher amount towards the front edge than towards the back edge as more absorbency is typically required towards the front half of the article. Typically the front and back edges 280, 282 may be shorter than the longitudinally-extending side edges 284, 286. The absorbent core also comprises a top side 288 and a bottom side 290. The top side of the core is the side placed or intended to be placed towards the topsheet 24 of the article and the bottom side is the side placed or intended to be placed towards the backsheet 25 in the finished article. The top side of the core wrap may be treated to be more hydrophilic than the bottom side.

The absorbent core's footprint is typically generally rectangular with a width W' in the transversal direction and a length L' in the longitudinal direction as measured from edge to edge, including the region of the core wrap which does not enclose the absorbent material, in particular at the front end seal 280' and the back end seal 282' when present. If the core is not rectangular, the maximum dimension measured along the transversal direction and the longitudinal direction can be used to report the width and length of the core respectively. The width and length of the core may vary depending on the intended usage. For baby and infant diapers, the width W' may for example in the range from 40 mm to 200 mm and the length L' from 100 mm to 600 mm. Adult incontinence products may have higher maximum dimensions.

The absorbent core can notionally (i.e. virtually) comprise a longitudinal axis 80 extending from the front edge 280 to the back edge 282 and dividing the core in two substantially symmetrical halves relative to this axis, when viewing the core in the plane formed by the longitudinal and transversal direction (x, y). The longitudinal axis of the core and the longitudinal axis of the article are typically superposed in the vertical direction perpendicular to the plane of the core and the article.

The absorbent material 60 may be any conventional absorbent material used in absorbent articles. Absorbent cores have been traditionally comprised as absorbent material a blend of cellulose fibers with superabsorbent polymer (SAP) particles, also called absorbent gelling materials (AGM), see for example U.S. Pat. No. 5,151,092 (Buell). The absorbent material of the core of the invention may be any known absorbent material known in the art, but will typically comprise or consist of superabsorbent polymers (herein referred to as "SAP"). The SAP may be typically in particulate forms (superabsorbent polymer particles), optionally mixed with cellulose fibers, but it not excluded that other forms of SAP may be used such as a superabsorbent polymer foam for example. The SAP useful in the present invention includes a variety of water-insoluble, but water-swellable polymers capable of absorbing large quantities of fluids. The term "superabsorbent polymer" refers herein to absorbent materials, which may be cross-linked polymeric materials, that can typically absorb at least 10 times their weight of an aqueous 0.9% saline solution as measured using the Centrifuge Retention Capacity (CRC) test (EDANA method WSP 241.2.R3 (12). The SAP may in particular have a CRC value of more than 20 g/g, or more than 24 g/g, or of from 20 to 50 g/g, or from 20 to 40 g/g, or 24 to 30 g/g. The absorbent cores may also consist essentially of SAP without cellulose fibers as absorbent material (so called "airfelt-free" cores) as known in the art. For example WO2008/155699 (Hundorf) discloses absorbent cores with a patterned layer of SAP immobilized by a net of fibrous thermoplastic adhesive material deposited over the layer of SAP. The fibrous thermoplastic material helps maintaining the SAP in position within the absorbent core prior to and during use of the article, without substantially restricting the ability of the SAP to absorb large volumes of urine. More recently, WO2012/170783 (Hundorf et al.) discloses absorbent cores comprising absorbent material having a basis weight that varies across the absorbent core.

The absorbent material may consist of SAP particles immobilized by an adhesive to provide a relatively thin core. The absorbent core may thus be relatively thin, in particular thinner than conventional cores comprising cellulosic fibers. In particular, the caliper of the core (dry, i.e. before use) as measured at the centerpoint point (C) or at any other points of the surface of the core according may be from 0.25 mm to 5.0 mm, in particular from 0.5 mm to 4.0 mm as measured at 2.07 kPa (0.30 psi) of pressure using the same setting as for the Absorbent Article Caliper Test described below. However other types of absorbent material are more commonly used, the absorbent material may be in particular a mix of cellulose fibers and SAP particles.

The absorbent material 60 may be deposited within the core wrap as one layer, or as two absorbent layers applied on the top substrate 16 and bottom substrate 16' respectively in a pattern of land areas separated by junction areas. This advanced way of making cores free of cellulose fibers is for example generally disclosed in WO2008/155699. In particular, two absorbent layers having offset land and junction areas may be combined to form an absorbent material deposition area in which the absorbent material is substantially continuous. If the absorbent core is made according to this process, it may further advantageously comprise a fibrous thermoplastic adhesive to further immobilize the absorbent material. However the absorbent cores of the present invention are not limited to a particular process for making them, and the cores of the invention may be more conventionally by air-laying a mix of cellulose fibers and superabsorbent particles on a conventional air-laying drum.

The absorbent material 60 defines an absorbent material deposition area within the core wrap that delimits the area including absorbent material is present, including the channel-forming areas, as seen from above within the plane of the core. The deposition area may be generally rectangular as shown in the FIG. 6, or may be shaped so that it has a tapered section in the crotch region, as is known in the art in so-called shaped cores.

Channel-Forming Areas 26

The absorbent core may comprise within the absorbent material deposition area at least one, and in particular a first longitudinally-extending area 26a and a second longitudinally-extending area 26b, which are areas substantially free of absorbent material and are each disposed on opposite side of the longitudinal axis. These areas are designated herein as channel-forming areas 26a, 26b. Substantially free means that some minor amount of absorbent material that were not planed but may be involuntary deposited during a fast making process may be present.

The channel-forming areas may be typically mirror image of each other relative to the longitudinal axis. The channel-forming areas 26 are longitudinally-extending, meaning that each zone extends at least as much in the longitudinal direction than in the transversal direction, and typically at least twice as much in the longitudinal direction than in the transverse direction (as measured after projection on the respective axis). The channel-forming areas 26 may have a length Lc projected on the longitudinal axis 80 of the core that is at least 10% of the length L' of the absorbent core, in particular from 20% to 80% of the length L' of the core. The absorbent material-free channel-forming areas may have a width Wc along at least part of their length which is at least 2 mm, or at least 3 mm or at least 4 mm, up to for example 20 mm, or 16 mm or 12 mm. The width Wc of each areas substantially free of absorbent material may be constant through substantially its whole length or may vary along its length.

The top side 288 of the core wrap may be advantageously bonded to the bottom side 290 of the core wrap through these channel-forming areas 26 by a bond 27, as illustrated on FIG. 7. The bonds 27 may be provided by an auxiliary glue (not represented) applied directly to the inner surface of at least one of the substrate, and/or by any other bonding means such as fusion bonding or ultra-sonic bonding. Typically the bonds 27 may generally have the same outline and shape as the channel-forming areas 26 in which they are contained, but may be slightly smaller to allow for a safety margin (e.g. by a few mm) as some deviations from the optimal registration may happen during high speed process. It is however not excluded that the channel bonds 27 may be provided in areas containing absorbent material, in those cases the bonds may however be substantially less strong and more easily delaminate when the absorbent material swells. The channel-forming areas 26 may be also be provided without such bonds, but then the absorbent material may relatively quickly fill into these areas so that the fluid handling properties of the channels may be relatively quickly compromised.

As the absorbent material 60 swells when it absorbs a liquid such as urine, the bond 27 in the channel-forming areas 26 remain at least initially in place between the top and bottom sides of the core wrap, so that the channel-forming areas 26 form easily recognizable three-dimensional channels. These three-dimensional channels may further cooperate with the channels of the distribution layer 54 disposed above the absorbent core 28 to guide the fluid inside the core and longitudinally towards the front and back of the article.

The channel-forming areas 26 of the core may extend longitudinally further than the channels 86 of the intermediate (distribution) layer, but the channels and channel-forming areas may be otherwise superposed along their length. More generally, the channels 86 of the intermediate layer may be superposed in the vertical direction with the channel-forming areas 26 of the core for at least 50% of the channel's length, or at least 60%, 70%, 80% and up to 100% of the length of the channels. Typically the absorbent core may be longer and wider than the intermediate layer, so that the channel-forming areas can extend further than the channels of the intermediate layer. It may be advantageous that the channels 86 and/or the channel-forming areas 26 do not reach any of the edges of the layer in which they are formed, to reduce the risk of fluid escaping the layer. Thus the channel-forming areas 26 in the core, as well as the channel 86 in the intermediate layer, may be designed to stop at a distance of at least 5 mm from any edges of the layer in which they are formed. It is however also not excluded that the distribution layer may be as wide and/or as long as the absorbent core, and the channels and the channel-forming areas may have similar dimensions. It is also not excluded that the channel-forming areas 26 of the core when present are not superposed with the channels 86 of the distribution layer 54.

Core Wrap 16, 16'

The absorbent core comprises a core wrap which encloses the absorbent material. The core wrap can typically comprise a substrate for receiving the absorbent material when the core is made. Various core wrap constructions are possible. The core wrap may in particular comprise as represented in the Figures two separate substrates 16, 16' forming the top side and the bottom side of the core wrap respectively. Having two different substrates for example allows separately depositing about half of the absorbent material on each substrate before combining these to form the core wrap. The two substrates may be attached in a C-wrap configuration with two longitudinal seals 284', 286', and optionally a front seal 280' and a back seal 282'. However this core wrap construction is not limiting of the invention, as any conventional core wrap construction may also be used, for example a single substrate on a portion of which the absorbent material is deposited and then the rest of the substrate folded over the deposited absorbent material to form the other side of the core. This single substrate construction can then be sealed longitudinally with a single longitudinal edge seal. The core wrap may also comprise two substrates disposed flat in a face to face relation (sandwich).

The substrates may be formed by any materials suitable for receiving and containing the absorbent material. Typical substrate materials used in the production of conventional cores may be used, in particular paper, tissues, films, wovens or nonwovens, or laminate of any of these. The core wrap may in particular be formed by a nonwoven web, such as a carded nonwoven, spunbond nonwoven ("S") or meltblown nonwoven ("M"), and laminates of any of these. For example spunmelt polypropylene nonwovens are suitable, in particular those having a laminate web SMS, or SMMS, or SSMMS, structure, and having a basis weight range of about 5 gsm to 15 gsm. Suitable materials are for example disclosed in U.S. Pat. No. 7,744,576, US 2011/0268932A1, US2011/0319848A1 and US2011/0250413A1. Nonwoven materials are typically made of synthetic fibers, such as PE, PET and in particular PP fibers. It is also possible than the core wrap may be at least partially formed from a component of the article having another function than substrate for the absorbent material. For example, it is possible that the backsheet may form the bottom side of the core wrap and/or that a distribution layer or the topsheet may form the top side of the core wrap. However, typically the core wrap is made of one or more substrates whose only function is to receive and enclose the absorbent material, as indicated previously.

As used herein, the terms "nonwoven layer" or "nonwoven web" generally means a manufactured sheet, web or batt of directionally or randomly orientated fibers, bonded by friction, and/or cohesion and/or adhesion, excluding paper and products which are woven, knitted, tufted, stitch-bonded incorporating binding yarns or filaments, or felted by wet-milling, whether or not additionally needled. The fibers may be of natural or synthetic origin and may be staple or continuous filaments or be formed in situ. Commercially available fibers have diameters ranging from less than about 0.001 mm to more than about 0.2 mm and they come in several different forms such as short fibers (known as staple, or chopped), continuous single fibers (filaments or monofilaments), untwisted bundles of continuous filaments (tow), and twisted bundles of continuous filaments (yam). Nonwoven webs can be formed by many processes such as meltblowing, spunbonding, solvent spinning, electrospinning, carding and airlaying. The basis weight of nonwoven webs is usually expressed in grams per square meter (g/m2 or gsm).

As illustrated in FIG. 7, a first substrate 16 may substantially form the whole of the top surface 288 of the core wrap and a second substrate 16' substantially form the whole of the bottom surface 290 of the core wrap, but it is not excluded that this may be the other way round. By "substantially forming the whole of the surface" it is meant that the outwardly extending flaps of the other substrate that have been folded longitudinally may also form part of the surface considered. As seen in FIG. 7, the first substrate 16 may comprise two side flaps laterally extending along the length of the core and which are folded inwardly over each side edge 284, 286 of the absorbent core. The flaps may be attached to the outer surface of the second substrate 16' for example by using an adhesive seal along each C-wrap seal 284', 286'. One or two continuous or semi-continuous lines of glue may be typically applied along the length of the flaps to bond the inner surface of the flaps to the external surface of the other substrate.

The core may also comprise so-called sandwich seals 280', 282' where the two substrates are bonded along one edge of the core to each other in face-to-face relationship with the inner surface of each substrate bonded to the inner surface of the other substrate. These sandwich seals can for example be formed using a hotmelt glue applied in a series of stripes in a direction perpendicular of the edge. The end seals are however optional as many absorbent cores are left open at the front and back ends.

Auxiliary Glue

An auxiliary glue within the core is optional. When present, the auxiliary glue may be applied directly over the inner surface of the top side and/or bottom side of the core wrap. The auxiliary glue may at least partially form the bonds 27 between the two sides of the core wrap, through the areas substantially free of absorbent material of the channel-forming areas. The auxiliary glue may also be useful to improve the adhesion between the inner surface of the core wrap and the absorbent material. A fibrous thermoplastic material may also be present within the core wrap to help immobilizing the AGM particles, especially if the core is free of cellulose fibers.

Exemplary Method and Apparatus for Making the Absorbent Core

The absorbent cores may be made by any conventional methods known in the art that allow a relative precise and controlled deposition of absorbent material. The articles may be hand-made or industrially produced at high speed on a modern converting line. As mentioned above, the absorbent core can for example be made industrially by combining two absorbent structures using the SAP printing method first disclosed in WO2008/155699 (Hundorf et al.) and further developed in WO2012/170798A1 (Jackels et al.), with the adaptations required to obtain the desired distribution of the absorbent material. The absorbent core may also be made by a conventional fiber/SAP deposition process in a drum.

Example of Article in a Pant Form

As indicated previously, the invention may be also used in absorbent articles presented in the form of a pant or underwear (herein "pant"). In these articles, the waist and the leg openings are pre-formed during manufacture so that the article can be put on like underwear. These pant articles typically have a front waist panel and a back waist panel which are sealed together via side seams. The side seams can be broken to remove and discard the article and are typically not re-fastenable. The front and back waist panels are typically elasticized. Pants are used as taped diapers on babies and younger children for day wear and for overnight dryness, as training pant for older children at the toilet training stage, and also as adult incontinence protection.

The outline of such a pant article is schematically illustrated in perspective on FIG. 8. The pant comprises a front waist panel 110 and a back waist panel 120 shown in dotted lines. The front and back waist panels are joined together at side seams (not represented) to form the waist opening and the leg openings. The waist panels are typically elasticized, either using a material which is inherently elastic to make them (such as a laminate comprising an elastomeric layer between two nonwoven layers) or by sandwiching a plurality of elastic strands 130 between two nonwovens along the width of the panels, as is known in the art. The pants may further comprise a chassis comprising the remaining components of the article, in particular the topsheet 24, the backsheet 25, the absorbent core 28 and barrier cuffs 30 including upstanding barrier leg cuffs. These components may be generally constructed as in previously disclosed for the taped diaper.

FIG. 9 shows a top view of the wearer-facing side of the pant with the side seams opened and the pant flattened out. For clarity of the view, the barrier cuffs 30, the topsheet 24 and an acquisition layer are not shown in FIG. 9. These and the components represented may be generally as previously discussed. For example, the distribution layer 54 comprises a pair of material-free channel areas 86 which can be superposed with a pair of generally parallel channel-forming areas 26 in the absorbent core. The channels in the distribution layer may be typically shorter or have the same length as the channel-forming areas 26 in the core. Of course, many other constructions for pants are known in the art and possible to use in the present invention.

Having described in details the key features of the invention, the following sections provide more details on some of the typical components found in absorbent articles. The materials described below are of course optional and non-limiting, unless explicitly indicated otherwise.

Topsheet 24

The topsheet typically forms the majority of the wearer-contacting surface of the article and is the first layer that the body exudates contact. The topsheet is preferably compliant, soft-feeling, and non-irritating to the wearer's skin. Further, at least a portion of the topsheet is liquid permeable, permitting liquids to readily penetrate through its thickness. Any known topsheet may be used in the present invention. A suitable topsheet may be manufactured from a wide range of materials. Most topsheets are nonwoven materials or apertured formed films, but other materials are possible such as porous foams, reticulated foams, woven materials. Typical diaper topsheets have a basis weight of from about 10 gsm to about 28 gsm, in particular between from about 12 gsm to about 18 gsm but higher basis weights are possible if it is desired to provide a very soft feeling wearer-contacting surface for example.

Nonwoven topsheets may be made of natural fibers (e.g., wood or cotton fibers), synthetic fibers or filaments (e.g. polyester or polypropylene or bicomponent PE/PP fibers or mixtures thereof), or a combination of natural and synthetic fibers. If the topsheet includes nonwoven fibers, the fibers may be spunbond, carded, wet-laid, meltblown, hydroentangled, or otherwise processed as is known in the art. In particular the topsheet may be a spunbond PP nonwoven. A suitable topsheet comprising a web of staple-length polypropylene fibers is manufactured by Veratec, Inc., a Division of International Paper Company, of Walpole, Mass. under the designation P-8.

The topsheet may of the type comprising a plurality of apertures. At least some of the apertures may have an area ranging from 1 mm2 to 20 mm2, and the topsheet may in particular comprise on average from 1 to 20 apertures per cm2. The aperture ratio (the surface of all the apertures divided by the overall surface of the topsheet, measured when the topsheet is in a relaxed state, i.e. with just enough tension to smooth out any wrinkles) is advantageously in the range from 10% to 45%, in particular from 25% to 40%, more particularly from 30% to 35%. Typically, the total area of the apertures at the surface of a diaper may have an area of between about 10 cm2 and about 50 cm2, in particular between about 15 cm2 and 35 cm2. Examples of apertured topsheet are disclosed in U.S. Pat. No. 6,632,504 (Gillespie et al.).

WO 2011/163582 (Rinnert et al.) also discloses a suitable colored nonwoven topsheet having a basis weight of from 12 to 18 gsm and comprising a plurality of bonded points. Each of the bonded points has a surface area of from 2 mm2 to 5 mm2 and the cumulated surface area of the plurality of bonded points is from 10 to 25% of the total surface area of the topsheet.

Suitable formed film topsheets are also described in U.S. Pat. Nos. 3,929,135, 4,324,246, 4,342,314, 4,463,045, and 5,006,394. Other suitable topsheets may be made in accordance with U.S. Pat. Nos. 4,609,518 and 4,629,643. Such formed films are available from The Procter & Gamble Company of Cincinnati, Ohio as "DRI-WEAVE" and from Tredegar Corporation, based in Richmond, Va., as "CLIFF-T". The topsheet may also have a three-dimensional appearance and feel, or there may be an additional, smaller, three-dimensional layer placed on top of the topsheet. Such three-dimensional additional layers may be for example particularly useful to receive low viscous exudates such as the stool of young babies Examples of such fluid entangled dual layered three-dimensional materials and processes to obtain them have been disclosed for example in US2014/0121623A1, US2014/0121621A1, US2014/0121624A1, US2014/0121625A1.

The topsheet may also be treated with a wetting agent to make it more hydrophilic. The wetting agent may be a surfactant as is known in the art. Other possible treatments are for example special coating by nanoparticles, as for example described in U.S. Pat. Nos. 6,645,569, 6,863,933, US2003/148684 and US2005/008839 (Cramer et al.) and U.S. Pat. No. 7,112,621 (Rohrbaugh et al). Any portion of the topsheet may also coated with a lotion as is known in the art. Examples of suitable lotions include those described in U.S. Pat. Nos. 5,607,760, 5,609,587, 5,643,588, 5,968,025 and 6,716,441. The topsheet may also include or be treated with antibacterial agents, some examples of which are disclosed in WO95/24173. Further, the topsheet, the backsheet or any portion of the topsheet or backsheet may be embossed and/or matte finished to provide a more cloth like appearance.

Backsheet 25

The backsheet may be any backsheet known in the art for absorbent articles. The backsheet may be positioned directly adjacent the garment-facing surface of the absorbent core. The backsheet prevents, or at least inhibits, the exudates absorbed and contained therein from soiling articles such as bedsheets and undergarments. The backsheet is typically impermeable, or at least substantially impermeable, to liquids (e.g., urine). The backsheet may, for example, be or comprise a thin plastic film such as a thermoplastic film having a thickness of about 0.012 mm to about 0.051 mm. The basis weight of those films is usually as low as possible to save material costs, typically from 10 gsm to 30 gsm, in particular below 20 gsm. A covering low basis weight nonwoven may be attached to the external surface of the film to provide for a softer touch.

Suitable backsheet materials include breathable materials which permit vapors to escape from the absorbent article while still preventing, or at least inhibiting, exudates from passing through the backsheet. Example breathable materials may include materials such as woven webs, nonwoven webs, composite materials such as film-coated nonwoven webs, microporous films such as manufactured by Mitsui Toatsu Co., of Japan under the designation ESPOIR NO and by Tredegar Corporation of Richmond, Va., and sold under the designation EXAIRE, and monolithic films such as manufactured by Clopay Corporation, Cincinnati, Ohio under the name HYTREL blend P18-3097.

The film may include at least about 20 weight percent filler particles, for example filler particles that include calcium carbonate, so that wherein the film has been stretched in the machine direction, e.g. to at least about 150 percent, fractures are formed where said filler particles are located. The films may be biaxially stretched at least about 150 percent in the machine direction and a transverse direction to cause fractures to form where said filler particles are located. Breathable films may generally have Water Vapor Transmission Rates (WVTR) in excess of 300 grams per square meter per 24 hours. The WVTR may be measured by the Desiccant Method as indicated in ASTM E96/E96M-14.

U.S. Pat. No. 6,075,179 for example discloses a suitable multilayer film comprising: a core layer made from an extrudable thermoplastic polymer, the core layer having a first exterior surface and a second exterior surface, a first skin layer attached to the first exterior surface of said core layer to form the multilayer film, the multilayer film defining an overall thickness. The first skin layer defines a first skin thickness, and comprising less than about ten percent of said overall thickness. The overall thickness is not exceeding about 30 micrometers and the multilayer film is a liquid barrier and has a WVTR of at least 300 g/m2/24 hours.

The backsheet may further typically comprise a nonwoven on its most external side to improve softness. Exemplary laminates comprising a breathable film and a nonwoven layer are for example disclosed in WO2014/022,362A1, WO2014/022,652A1 and U.S. Pat. No. 5,837,352. The nonwoven web may in particular comprise a spunbond nonwoven web and/or a laminate of a spunbond nonwoven web and a meltblown nonwoven web. The laminate may also have a water vapor transmission rate of at least 300 g/m2/24 hours. U.S. Pat. No. 5,843,056 for example discloses substantially liquid impermeable, vapor permeable composite backsheet.

Acquisition Layer 52

The absorbent article may comprise an acquisition layer 52, whose function is to quickly acquire the fluid away from the topsheet so as to provide a good dryness for the wearer. The acquisition layer is typically placed directly under the topsheet. The distribution layer 54 may be at least partially disposed under the acquisition layer. The acquisition layer may typically be or comprise a nonwoven material, for example a SMS or SMMS material, comprising a spunbonded, a melt-blown and a further spunbonded layer or alternatively a carded chemical-bonded nonwoven. The nonwoven material may in particular be latex bonded. Exemplary upper acquisition layers are disclosed in U.S. Pat. No. 7,786,341. Carded, resin-bonded nonwovens may be used, in particular where the fibers used are solid round or round and hollow PET staple fibers (50/50 or 40/60 mix of 6 denier and 9 denier fibers). An exemplary binder is a butadiene/styrene latex. Nonwovens have the advantage that they can be manufactured outside the converting line and stored and used as a roll of material. Further useful nonwovens are described in U.S. Pat. No. 6,645,569 (Cramer et al.), U.S. Pat. No. 6,863,933 (Cramer et al.), U.S. Pat. No. 7,112,621 (Rohrbaugh et al.), US2003/148684 (Cramer et al.) and US2005/008839 (Cramer et al.). The acquisition layer may be stabilized by a latex binder, for example a styrene-butadiene latex binder (SB latex). Processes for obtaining such latices are known, for example, from EP 149880 (Kwok) and US 2003/0105190 (Diehl et al.). The binder may typically be present in the acquisition layer in amount ranging from about 12% to about 50%, for example about 30%, by total weight of the acquisition layer. SB latex is available under the trade name GENFLO™ 3160 (OMNOVA Solutions Inc.; Akron, Ohio).

Another typical acquisition layer, sometimes referred to as secondary topsheet, may for example be a through-air bonded carded web ("TABCW") but many other alternatives material are known in the art and may be used instead. "Bonded carded web" refers to webs that are made from staple fibers that are sent through a combing or carding unit, which breaks apart and aligns the staple fibers in the machine direction to form a generally machine direction-oriented fibrous nonwoven web. This web is then drawn through a heated drum, creating bonds throughout the fabric without applying specific pressure (thru air bonding process). The TABCW material provides a low density, lofty through-air bonded carded web. The web may for example have a specific weight basis level at about 15 gsm to about 120 gsm (gram per m2), in particular about 30 gsm to about 80 gsm. The TABCW material can for example comprise about 3 to about 10 denier staple fibers. Examples of such TABCW are disclosed in WO2000/71067 (KIM DOO-HONG et al.). TABCW are available directly from all usual suppliers of nonwoven webs for use in absorbent articles, for example Fitesa Ltd or Fiberweb Technical Nonwovens.

A further acquisition layer (not shown) may be used in addition to the first acquisition layer described above. For example a tissue layer may be placed between the first acquisition layer and the distribution layer. The tissue may have enhanced capillarity distribution properties compared to the acquisition layers described above. The tissue and the first acquisition layer may be of the same size or may be of different size, for example the tissue layer may extend further in the back of the absorbent article than the first acquisition layer. An example of a hydrophilic tissue is a 13 to 15 gsm high wet strength tissue made of cellulose fibers from supplier Havix.

The intermediate layer according to the invention may also be an acquisition layer as discussed above.

Fastening System 42, 44

The absorbent article may include a fastening system, especially when the article is a taped diaper as exemplified in FIG. 1. The fastening system can be used to provide lateral tensions about the circumference of the absorbent article to hold the absorbent article on the wearer. Such a fastening system is not necessary for pant articles such as training pants and adult incontinence pants since the waist region of these articles is already bonded and elasticized. The fastening system usually comprises a fastener 42 such as tape tabs, hook and loop fastening components, interlocking fasteners such as tabs & slots, buckles, buttons, snaps, and/or hermaphroditic fastening components, although any other known fastening means are generally acceptable. A landing zone 44 is normally provided on the front waist region of the article for the fastener 42 to be releasably attached. Some exemplary surface fastening systems are disclosed in U.S. Pat. Nos. 3,848,594, 4,662,875, 4,846,815, 4,894,060, U.S. Pat. Nos. 4,946,527, 5,151,092 and 5,221,274 (Buell). An exemplary interlocking fastening system is disclosed in U.S. Pat. No. 6,432,098. The fastening system may also provide a means for holding the article in a disposal configuration as disclosed in U.S. Pat. No. 4,963,140 (Robertson et al.)

The fastening system may also include primary and secondary fastening systems, as disclosed in U.S. Pat. No. 4,699,622 to reduce shifting of overlapped portions or to improve fit as disclosed in U.S. Pat. Nos. 5,242,436, 5,499,978, U.S. Pat. No. 5,507,86, and U.S. Pat. No. 5,591,152.

Front and Back Ears 46, 40

The absorbent article may comprise front ears 46 and back ears 40 as is known in the art in taped diapers. Absorbent articles in pant chassis are already sealed along the waist edges typically do not require front ears and back ears. The ears can be integral part of the chassis, for example formed from the topsheet and/or backsheet as side panel. Alternatively, as represented in FIG. 1, they may be separate elements attached by gluing and/or heat embossing. The back ears 40 are optionally stretchable to facilitate the attachment of the tabs 42 on the landing zone 44 and maintain the taped diapers in place around the wearer's waist. The front ears 46 may also be optionally elastic or extensible to provide a more comfortable and contouring fit.

Barrier Leg Cuffs 34 and Gasketing Cuffs 32

Absorbent articles such as taped diapers, training pants or adult incontinence pants may typically further comprise cuff components 30 that improve the fit of the article around the legs of the wearer. Such cuffs typically comprise barrier leg cuffs 34 and gasketing cuffs 32. The cuffs 30 may comprise a piece of material, typically a nonwoven, which is one side partially bonded to the article and on the other side can be partially raised away from the topsheet and thus stand up from the plane defined by the topsheet as shown for example in FIG. 3. Both parts of the cuffs may be advantageously elasticized. The raised part of the cuff components is referred to herein as barrier leg cuffs 34 and can provide improved containment of liquids and other body exudates approximately at the junction of the torso and legs of the wearer. The barrier leg cuffs 34 extend at least partially between the front edge and the back edge of the absorbent article on opposite sides of the longitudinal axis and are at least present adjacent to the center point C of the article.

The barrier leg cuffs 34 may be delimited by a proximal edge 37 joined to the rest of the article, typically the topsheet, and a free terminal edge 38 intended to contact and form a seal with the wearer's skin. The barrier leg cuffs 34 may be joined at the proximal edge 37 with the chassis of the article by a bond which may be made for example by adhesive bonding, fusion bonding or combination of known bonding means, for example as disclosed in WO2014/168810A1 (Bianchi et al.). The bond at the proximal edge 37 may be continuous or intermittent.

The barrier leg cuffs 34 can be integral with (i.e. formed from) the topsheet or the backsheet, or more typically be formed from a separate material joined to the rest of the article. Typically the material of the barrier leg cuffs may extend through the whole length of the article but is "tack bonded" to the topsheet towards the front edge and back edge of the article so that in these sections the barrier leg cuff material remains flush with the topsheet. Each barrier leg cuff 34 may comprise one, two or more elastic strings 35 close to its free terminal edge 38 to provide a better seal.

In addition to the barrier leg cuffs 34, the article may comprise gasketing cuffs 32, which are formed in the same plane as the chassis of the absorbent article, in particular may be at least partially enclosed between the topsheet and the backsheet, and typically placed further laterally outwardly relative to the barrier leg cuffs 34. The gasketing cuffs 32 can provide a better seal around the thighs of the wearer. Usually each gasketing leg cuff 32 will comprise one or more elastic string or elastic element 33 comprised in the chassis of the diaper for example between the topsheet and backsheet in the area of the leg openings. Typically the barrier leg cuffs 34 are disposed more internally than the gasketing cuffs 32. The barrier leg cuffs are thus also referred to as inner cuffs and the gasketing cuffs as outer cuffs.

For example, U.S. Pat. No. 3,860,003 describes a disposable diaper which provides a contractible leg opening having a side flap and one or more elastic members to provide an elasticized leg cuff (a gasketing cuff). U.S. Pat. No. 4,808,178 (Aziz) and U.S. Pat. No. 4,909,803 (Aziz) describe disposable diapers having "stand-up" elasticized flaps (barrier leg cuffs) which improve the containment of the leg regions. U.S. Pat. No. 4,695,278 (Lawson) and U.S. Pat. No. 4,795,454 (Dragoo) describe disposable diapers having dual cuffs, including gasketing cuffs and barrier leg cuffs. All or a portion of the barrier leg and/or gasketing cuffs may be treated with a lotion.

Other Components

The absorbent articles of the invention can further comprise any other typical components known for the intended purpose of the article that are not illustrated in the Figures, such as a transverse barrier element extending across the topsheet to form a receptacle for bowel movement, a lotion application on the topsheet, a wetness indicator comprising a pH indicator disposed between the absorbent core and the backsheet, etc. These components are well-known in the art and will not be further discussed herein. Reference is made to WO2014/093310 where several examples of these components are disclosed in more details.

The absorbent article may also comprise at least one elastic waist band (also called elastic waist feature) disposed parallel to and along the back edge of the article and less commonly parallel to and along the front edge of the article. Such waistbands help providing improved fit and containment at the back and/or front edge of the article. The elastic waist feature is generally intended to elastically expand and contract to dynamically fit the wearer's waist. The elastic waist feature may be constructed in a number of different configurations. Non-limiting examples of back and front waistbands can be found in WO2012/177400 and WO2012/177401 (Lawson), and U.S. Pat. Nos. 4,515,595, 4,710,189, 5,221,274 and 6,336,922 (VanGompel et al.).

Packages

A plurality of articles according to the invention may be packaged in a package for transport and sale. At least 50% of the articles in the package may be according to the invention, and preferably substantially all the articles. The articles may be folded and packaged as is known in the art. The package may be for example a plastic bag or a cardboard box. Diapers may typically bi-folded along the transversal axis and the ears folded inwardly before being packaged. The absorbent articles may be packed under compression so as to reduce the size of the packages, while still providing an adequate amount of absorbent articles per package. By packaging the absorbent articles under compression, caregivers can easily handle and store the packages, while also providing distribution and inventory savings to manufacturers owing to the size of the packages.

The absorbent articles may thus be packaged compressed at an In-Bag Compression Rate of at least 10%, in particular of from 10% to 50%, in particular from 20% to 40%. The "In-Bag Compression Rate" as used herein is one minus the height of a stack of 10 folded articles measured while under compression within a bag ("In-Bag Stack Height") divided by the height of a stack of 10 folded articles of the same type before compression, multiplied by 100; i.e. (1-In-Bag Stack Height/stack height before compression)*100, reported as a percentage. Of course, the stack in the bag does not need to have exactly 10 articles, rather the value measured for the height of stack of article in the package is divided by the number of articles in the stack and then multiplied by 10. The method used to measure the In-Bag Stack Height is described in further details in the Test Procedures. The articles before compression may be typically sampled from the production line between the folding unit and the stack packing unit. The stack height before compression is measured by taking 10 articles before compression and packing, and measuring their stack height as indicated for the IBSH.

Packages of the absorbent articles of the present disclosure may in particular have an In-Bag Stack Height of less than 110 mm, less than 105 mm, less than 100 mm, less than 95 mm, less than 90 mm, specifically reciting all 0.1 mm increments within the specified ranges and all ranges formed therein or thereby, according to the In-Bag Stack Height Test described herein. For each of the values indicated in the previous sentence, it may be desirable to have an In-Bag Stack Height of greater than 60, or greater than 70 mm, or greater than 75 mm, or greater than 80 mm. Alternatively, packages of the absorbent articles of the present disclosure may have an In-Bag Stack Height of from 60 mm to 110 mm, from 75 mm to 110 mm, from 80 mm to 110 mm, from 80 mm to 105 mm, or from 80 mm to 100 mm, specifically reciting all 0.1 mm increments within the specified ranges and all ranges formed therein or thereby, according to the In-Back Stack Height Test described herein.

Relations Between the Layers and Components

Typically, adjacent layers will be joined together using conventional bonding method such as adhesive coating via slot coating or spraying on the whole or part of the surface of the layer, or thermo-bonding, or pressure bonding or combinations thereof. Most of the bonding between components is for clarity and readability not represented in the Figure. Bonding between the layers of the article should be considered to be present unless specifically excluded. Adhesives may be typically used to improve the adhesion of the different layers, for example between the backsheet and the core wrap. The adhesives used may be any standard hotmelt glue as known in the art. The individual components may be converted into an absorbent article according to any of the processes known in the art.

Test Procedures

The values indicated herein are measured according to the methods indicated herein below, unless specified otherwise. All measurements are performed at 21° C.±2° C. and 50%±5% RH, unless specified otherwise. All samples should be kept at least 24 hours in these conditions to equilibrate before conducting the tests, unless indicated otherwise.

Centrifuge Retention Capacity (CRC)

The CRC measures the liquid absorbed by the superabsorbent polymer particles for free swelling in excess liquid. The CRC is measured according to EDANA method WSP 241.2.R3 (12).

Absorbent Article Caliper Test

This test is used to measure the caliper of the absorbent article (before use i.e. without fluid loading) in a standardized manner.

Equipment: Mitutoyo manual caliper gauge with a resolution of 0.01 mm, or equivalent instrument.

Contact Foot: Flat circular foot with a diameter of 17.0 mm (±0.2 mm). A circular weight may be applied to the foot (e.g., a weight with a slot to facilitate application around the instrument shaft) to achieve the target weight. The total weight of foot and added weight (including shaft) is selected to provide 2.07 kPa (0.30 psi) of pressure to the sample.

The caliper gauge is mounted with the lower surface of the contact foot in an horizontal plane so that the lower surface of the contact foot contacts the center of the flat horizontal upper surface of a base plate approximately 20×25 cm. The gauge is set to read zero with the contact foot resting on the base plate.

Ruler: Calibrated metal ruler graduated in mm.

Stopwatch: Accuracy 1 second.

Sample preparation: The article is conditioned at least 24 hours as indicated above.

Measurement procedure: The article is laid flat with the bottom side, i.e. the side intended to be placed towards the backsheet in the finished article facing down. The point of measurement (e.g. the center point C) is carefully drawn on the top side of the article taking care not to compress or deform the article.

The contact foot of the caliper gauge is raised and the article is placed flat on the base plate of the caliper gauge with the top side of the article up so that when lowered, the center of the foot is on the marked measuring point.

The foot is gently lowered onto the article and released (ensure calibration to "0" prior to the start of the measurement). The caliper value is read to the nearest 0.01 mm, 10±1 seconds after the foot is released.

Ten articles are measured in this manner for a given product and the average caliper is calculated and reported with an accuracy of one tenth mm.

If the absorbent articles were provided folded and/or in a package, the articles to be measured are unfolded and/or removed from the center area of the package. If the package contains more than 4 articles, the outer most two articles on each side of the package are not used in the testing. If the package contains more than 4 but fewer than 14 articles, then more than one package of articles is required to complete the testing. If the package contains 14 or more articles, then only one package of articles is required to perform the testing. If the package contains 4 or fewer articles then all articles in the package are measured and multiple packages are required to perform the measurement. Caliper readings should be taken 24±1 hours after the article is removed from the package, unfolded and conditioned. Physical manipulation of product should be minimal and restricted only to necessary sample preparation.

Any elastic components of the article that prevent the article from being laid flat under the caliper foot are cut or removed. These may include leg cuffs or waistbands. Pant-type articles are opened or cut along the side seams as necessary. Apply sufficient tension to flatten out any folds/wrinkles. Care is taken to avoid touching and/or compressing the area of measurement.

Water Retention Value Measurement Procedure

The following procedure is utilized to determine the water retention value of fibers using a centrifugal method. A sample of 0.35±0.05 grams of fibers is soaked in a covered container with 100 mL distilled water at 23±2° C. for 17 hours. The soaked fibers are collected on a filter and transferred to a US standard 80-mesh wire basket supported 40 mm above a 60-mesh screened bottom of a centrifuge tube. The tube is covered with a plastic cover and the sample is centrifuged at a relative centrifuge acceleration of 1600±100 gravities (15.7±1.0 km/s2) for 20 minutes. The centrifuged fibers are then removed from the basket and weighed. The weighed fibers are dried to a constant weight at 105° C. in a forced-air oven located in a controlled temperature and humidity environment at 23±2° C. and 50±5% RH. The water retention value (WRV) is calculated as follows:

$$WRV = \frac{(W-D)}{D} \times 100$$

where

W=wet weight of centrifuged fibers

D=dry weight of centrifuged fibers, and

W−D=weight of absorbed water

Lateral Compression Force Measurement Method

This test method is used to measure the lateral force required to compress the crotch region of an absorbent article such as a diaper in the transversal direction under specific conditions. In short, the waist region of the article is attached to a suspended cylinder as schematically illustrated on FIG. 10 so that the crotch region of the diaper hangs down. Two compressing plates are placed symmetrically on each transversal side of the crotch of the diaper. The plates are driven together by a motor and the force required to compress the crotch region of the diaper to a predetermined distance (40 mm) is measured. This test can be conducted on any wide range of articles, including any typical diapers in taped or pant format. The waist opening of the diaper should of course be sufficiently large to be attached to the cylinder.

Figure 10:
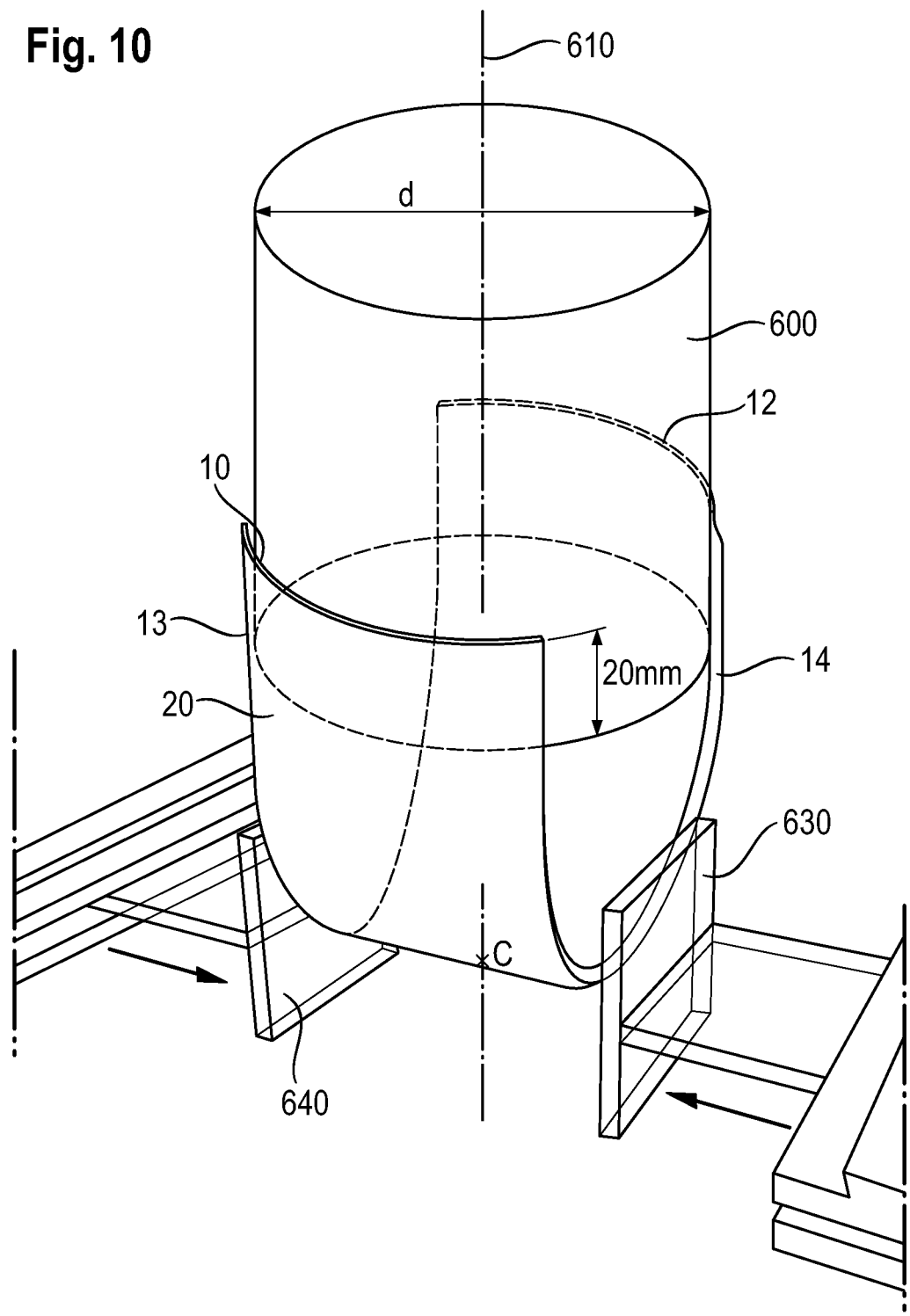
FIG. 10 shows an apparatus for measuring the Lateral Compression Force of an absorbent article.

The step-by-step instruction of this method is explained below together with the illustration on FIG. 10.

1. The test is sequentially conducted on at least five articles having the same construction to obtain an average value. If the articles are sampled from a packaging such as a plastic bag, the articles are sampled from the center of the bag, to avoid selecting damaged or crumbled articles which are sometimes present on the sides of the package due to damages during packing and transport.
2. The longitudinal axis 80 on each absorbent article is marked on the wearer-facing (inner) side of the article. The longitudinal axis generally divides the article into two roughly symmetric pieces along the length of the absorbent article when the article is viewed from the top as exemplarily shown on FIG. 1. Marking can be made with any pen taking care not to damage the article while marking.
3. The transversal axis 90 is marked on the same side of the absorbent article as the longitudinal axis 80. The intersection of the crotch line and the longitudinal axis is the centerpoint (or crotch) point C.
4. The absorbent article with its wearer-facing side facing up is then fixed on a rigid plastic cylinder as schematically represented in FIG. 10. The cylinder 600 has a diameter d of 150 mm (+−1 mm). The upper 20.0 mm (+−0.5 mm) of the front side 10 of the article is first attached to the external surface of the cylinder closest to the operator via a double sided tape previously applied on the lower edge of the cylinder, or via other fastening means, so that the absorbent article is securely and releasably attached to the lower edge of the cylinder. The upper 20.0 mm (+−0.5 mm) of the back side 12 of the article is similarly attached at the diametrically opposed external surface of the cylinder.
5. The cylinder is held rigidly such that it does not move during the test. One way to achieve this is to attached attach it to a carrier such as a lab foot with a holding arm (not represented) so that it does not move during the test.
6. The absorbent article is then laterally compressed as detailed below. Compressive forces are applied to the absorbent article by an assembly comprised of a pair of compression plates 630, 640, which simulate the portion of the legs compressing the absorbent article during use. Each compression plate have dimensions of 90 mm (+−1 mm)×90 mm (+−1 mm). The plates can be made from any rigid and smooth suitable material that can be formed into the required flat, square shape (e.g. aluminum, Plexiglas). The plates are placed lined up opposite one another. The compression plates are placed so that the transversal axis 90 on the wearer-facing side of the article and the geometrical center of each compression plate are linearly aligned in the horizontal plane.
7. The distance between the compression plates is initially of 140.0 mm+−0.5 mm, or more if the width of the article so requires so that the plates do not initially touch the article.

Each compression plate is driven toward the crotch point at constant rate of 400 mm/minute each. The final distance between the plates narrows to a final gap of 40.0 mm+−0.5 mm when the absorbent article is compressed and the compression force is measured. The equipment includes a force load cell on one of the plates with an appropriate measurement range e.g. from 0.01 N and up to 100 N of compressive force and a precision of within +/−0.01 N. The force variation during the compression step may be recorded by computer based program for the different samples. Such an apparatus and program is for example available from the company Zwick Roell GmbH based in Ulm, Germany. The data indicated herein were measured using a Zwick BX 1120.25 test apparatus but any similar apparatus working according to the principle indicated above may be used.

8. Once the absorbent article has been compressed to 40 mm, the compression plates are returned to their initial positions at the same speed as in step 7. The maximum force value recorded to the nearest 0.01 N during this first compression cycle for the tested article is the Lateral Compression Force for this article.

This procedure is repeated for 5 individual articles having the same construction and the results are averaged to obtain the Lateral Compression Force for a given article's construction.

Lotion-to-Channel Overlap Ratio

The lotion-to-channel overlap ratio may be directly calculated from the manufacturer's specification of the absorbent article, including the relative placement of the lotion pattern and the channels on the intermediate layer. If these specifications are not available because a third party product is analyzed, these dimensions can be also measured on the product directly. For this purpose, the outline of the channels can be marked using an appropriate pencil or marker directly on the topsheet. A light box can be used for this purpose on which the diaper is disposed and back lit from the backsheet side, as this may improve the contrast between the channel areas and the rest of the intermediate layer. The topsheet with the channel's contours marked thereon may then be removed from the rest of the article (e.g. using a freezing spray to unglue the adhesive). The marked area of the channels can then be measured, directly using for example a ruler, or after taking a digital picture and using any standard picture analysis software. The lotion pattern can be marked on the topsheet (the lotion is usually easily recognizable by visual contrast, especially on a black background). The areas of the lotion pattern overlapping with the channel areas can then be measured also directly with a ruler or a picture analysis software. The ratio of the two areas (lotion area superposed with the channel divided by the overall channel areas and multiplied by 100) provide the lotion-to-channel overlap ratio, expressed as a percentage. This procedure is repeated for 5 individual articles having the same construction to obtain an average value of the lotion-to-channel overlap ratio for a given article's construction.

In-Bag Stack Height Test

The In-Bag stack height of a package of absorbent articles is determined as follows:

Equipment: A thickness tester with a flat, rigid horizontal sliding plate is used. The thickness tester is configured so that the horizontal sliding plate moves freely in a vertical direction with the horizontal sliding plate always maintained in a horizontal orientation directly above a flat, rigid horizontal base plate. The thickness tester includes a suitable device for measuring the gap between the horizontal sliding plate and the horizontal base plate to within ±0.5 mm. The horizontal sliding plate and the horizontal base plate are larger than the surface of the absorbent article package that contacts each plate, i.e. each plate extends past the contact surface of the absorbent article package in all directions. The horizontal sliding plate exerts a downward force of 850±1 gram-force (8.34 N) on the absorbent article package, which may be achieved by placing a suitable weight on the center of the non-package-contacting top surface of the horizontal sliding plate so that the total mass of the sliding plate plus added weight is 850±1 grams. Such a testing apparatus is for example illustrated on FIG. 19 of US2008/0312624A1.

Test Procedure: Absorbent article packages are equilibrated at 21±2° C. and 50±5% relative humidity prior to measurement. The horizontal sliding plate is raised and an absorbent article package is placed centrally under the horizontal sliding plate in such a way that the absorbent articles within the package are in a horizontal orientation. Any handle or other packaging feature on the surfaces of the package that would contact either of the plates is folded flat against the surface of the package so as to minimize their impact on the measurement. The horizontal sliding plate is lowered slowly until it contacts the top surface of the package and then released. The gap between the horizontal plates is measured to within ±0.5 mm ten seconds after releasing the horizontal sliding plate. Five identical packages (same size packages and same absorbent articles counts) are measured and the arithmetic mean is reported as the package width. The "In-Bag Stack Height"=(package width/absorbent article count per stack)×10 is calculated and reported to within ±0.5 mm.

Misc

As used herein, the terms "comprise(s)" and "comprising" are open-ended; each specifies the presence of the feature that follows, e.g. a component, but does not preclude the presence of other features, e.g. elements, steps, components known in the art or disclosed herein. These terms based on the verb "comprise" should be read as encompassing the narrower terms "consisting essentially of" which excludes any element, step or ingredient not mentioned which materially affect the way the feature performs its function, and the term "consisting of" which excludes any element, step, or ingredient not specified. Any preferred or exemplary embodiments described below are not limiting the scope of the claims, unless specifically indicated to do so. The words "typically", "normally", "preferably", "advantageously", "in particular" and the likes also qualify features which are not intended to limit the scope of the claims unless specifically indicated to do so.

Unless indicated otherwise, the description and claims refer to the absorbent core and article before use (i.e. dry, and not loaded with a fluid) and conditioned at least 24 hours at 21° C.+/−2° C. and 50+/−5% Relative Humidity (RH).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article having a longitudinal axis extending in a longitudinal direction and a transversal axis extending in a transversal direction perpendicular to the longitudinal direction, wherein the absorbent article comprises:
   a fluid-permeable topsheet defining a wearer-facing side of the article;
   a lotion on the topsheet having a lotion pattern covering a lotion pattern area;
   a fluid-impermeable backsheet defining a garment-facing side of the article;

an absorbent core between the topsheet and the backsheet, wherein the absorbent core comprises an absorbent material in a core wrap, the core wrap defining a footprint in a plane parallel to the longitudinal direction and the transversal direction;

an intermediate layer between the topsheet and the absorbent core, the intermediate layer comprising one or more longitudinally-extending channel(s), wherein the topsheet is depressed in the channel(s) such that an interior surface defining the channel(s) is abutted and such that an underlying absorbent core surface is abutted so that the wearer-facing side of the article has at least one depression corresponding to at least one of the underlying channel(s);

wherein the absorbent article comprises a lotion-to-channel overlap ratio defined as an area of the channel(s) of the intermediate layer overlapping with the lotion pattern divided by an overall area of the channel(s), and wherein the lotion-to-channel overlap ratio ranges from about 0% to about 20% of the area of the channel(s).

2. An absorbent article according to claim 1, wherein the lotion-to-channel overlap ratio ranges from about 0% to about 15%.

3. An absorbent article according to claim 1, wherein a ratio of the lotion pattern area relative to an area of the footprint of the absorbent core ranges from about 5% to about 25%.

4. An absorbent article according to claim 1, wherein the lotion pattern comprises longitudinally-oriented stripes.

5. An absorbent article according to claim 4, wherein the lotion pattern comprises from 2 to 10 longitudinally-extending stripes of lotion.

6. An absorbent article according to claim 4, wherein the lotion pattern comprises from 3 to 8 stripes of lotion.

7. An absorbent article according to claim 4, wherein the lotion pattern comprises from 4 to 6 stripes.

8. An absorbent article according to claim 4, wherein the longitudinally-extending stripes have a width of from 1 mm to 12 mm.

9. An absorbent article according to claim 1, wherein the lotion pattern does not extend beyond the footprint of the absorbent core.

10. An absorbent article according to claim 1, wherein the intermediate layer comprises a fibrous layer which has an average basis weight of at least 50 g/m2, wherein the average basis weight is calculated by dividing a weight amount of fibers present in the fibrous layer by an area of the intermediate layer where the fibers are present, excluding the areas of the channel(s) in the intermediate layer.

11. An absorbent article according to claim 10, wherein the fibrous layer comprises cross-linked cellulose fibers.

12. An absorbent article according to claim 1, wherein the channels of the intermediate layer are substantially free of intermediate layer material.

13. An absorbent article according to claim 1, wherein the topsheet is bonded directly or indirectly to the absorbent core through the channel(s) in the intermediate layer.

14. An absorbent article according to claim 1, wherein the topsheet is adhesively directly or indirectly bonded to the absorbent core through the channel(s) in the intermediate layer.

15. An absorbent article according to claim 1, wherein the one or more longitudinally-extending channels comprises a first longitudinally-extending channel and a second longitudinally-extending channel disposed symmetrically relative to the longitudinal axis.

16. An absorbent article according to claim 15, wherein a distance between the first and the second longitudinally-extending channels is at least 10 mm as measured along the transversal axis.

17. An absorbent article according to claim 1, wherein the absorbent core further comprises a pair of longitudinally-extending channel-forming areas disposed symmetrically relative to the longitudinal axis.

18. An absorbent article according to claim 17, wherein the channel-forming areas of the absorbent core are substantially free of absorbent material, and a top side of the core wrap is attached to a bottom side of the core wrap through the channel-forming areas of the absorbent core.

19. An absorbent article according to claim 17, wherein the pair of channel-forming areas of the absorbent core are at least partially superposed in the vertical direction with a first and second channels of the intermediate layer.

20. An absorbent article according to claim 1, wherein the absorbent material of the absorbent core is free of cellulose fibers.

* * * * *